United States Patent
Tamura et al.

(12) 
(10) Patent No.: US 6,541,470 B1
(45) Date of Patent: Apr. 1, 2003

(54) 1,2-DISUBSTITUTED 1,4-DIHYDRO-4-OXOQUINOLINE COMPOUNDS

(75) Inventors: Takashi Tamura, Takatsuki (JP); Haruo Kuriyama, Katano (JP); Masanobu Agoh, Kawanishi (JP); Yumi Agoh, Kawanishi (JP); Manabu Soga, Ashiya (JP); Teruyo Mori, Matsubara (JP)

(73) Assignee: Maruishi Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/649,596

(22) Filed: Aug. 29, 2000

(30) Foreign Application Priority Data

| Aug. 30, 1999 | (JP) | 11-242700 |
| Aug. 30, 1999 | (JP) | 11-242701 |
| Sep. 17, 1999 | (JP) | 11-262883 |
| Sep. 17, 1999 | (JP) | 11-262884 |

(51) Int. Cl.$^7$ .................. C07D 215/16; A61K 31/47; A61P 31/12
(52) U.S. Cl. .............. 514/228.2; 544/363; 544/128; 544/62; 546/153; 514/312; 514/253.07; 514/235.2; 514/228.2
(58) Field of Search ............ 546/153; 514/312, 514/253.07, 235.2, 228.2; 544/363, 128, 62

(56) References Cited

U.S. PATENT DOCUMENTS 4,284,629 A * 8/1981 Grohe et al. ................ 424/246
5,081,121 A * 1/1992 Osawa et al. ................ 514/312

FOREIGN PATENT DOCUMENTS

| GB | 835474 | * 5/1960 |
| WO | 0811613 | * 6/1997 |

OTHER PUBLICATIONS

CAS printout for Grohe et al.*
Coppola et al. J. Heterocyclic Chem. 16: 1605–1610.*
CAS printout for Van Es et al.*
CAS printout for Ito et al.*
CAS printout for Brana et al.*
CAS printout for Wentland et al.*
CAS printout for Guilhon et al.*
CAS printout for Venugopalan et al.*
CAS printout for Delle Monache et al.*
CAS printout for Wu et al.*
CAS printout for Grobe et al.*
CAS printout for Coppola et al.*
CAS printout for Avramova et al.*

* cited by examiner

Primary Examiner—Mukund J. Shah
Assistant Examiner—Hong Liu
(74) Attorney, Agent, or Firm—Millen, White, Zelano & Branigan, P.C.

(57) ABSTRACT

The present invention relates to substituted 1,4-dihydro-4-oxoquinolines having antiviral activity. The substituents are present at positions 1, 2 and at least one of 5–8 positions of the quinoline ring.

1 Claim, No Drawings

1,2-DISUBSTITUTED 1,4-DIHYDRO-4-OXOQUINOLINE COMPOUNDS

FIELD OF THE INVENTION

This invention related to a group of 1,2-disubstituted 1,4-dihydro-4-oxoquinoline compounds and the use of said compounds as an antiviral agent.

BACKGROUND OF THE INVENTION

The enteroviruses, rhinoviruses and hepatovirus are three groups within the family Picornaviridae which cause a wide range of human viral disease. The enterovirus group comprises 67 distinct serotypes, including 3 strains of poliovirus, 23 group A and 6 group B coxsackieviruses, 31 echoviruses, and 4 the newer numbered enteroviruses. Enteroviruses cause a broader range disease syndrome including "summer flu", upper respiratory illness, acute hemorrhagic conjunctivitis, hand, foot and mouth disease, myocarditis, aseptic meningitis, and poliomyelitis. Hepatitis A virus (HAV) was provisionally classified as enterovirus type 72. However, later studies have demonstrated several characteristics that distinguish HAV from other picornaviruses. It is concluded that HAV is a unique member of the family Picornaviridae, resulting in its classification into a new genus, Hepatovirus. HAV is a common cause of both sporadic and epidemic acute hepatitis in humans, produces substantial morbidity. Among the agents of viral hepatitis, HAV is most prevalent, but it is clinically less important than the hepatitis B and C virus. The clinical manifestations of HAV infection in humans can vary greatly, ranging from asymptomatic infection, commonly seen in young children, to fulminant hepatitis, which in some cases can result in death.

Human rhinovirus (HRV), which include over 100 different serotypes are the most important etiological agents of the common cold. Infection of the upper respiratory tract by members of the HRV group represents perhaps the most common viral affliction of humans, accounting for some 40 to 50% of common colds. Although HRV-induced upper respiratory illnesses often mild and self-limiting, severe disease can occur in subjects predisposed to respiratory problems, such as asthmatics. From an economic standpoint, rhinovirus infections of humans represent a significant health problem in terms of numbers of physicians' office visits, costs associated with symptomatic treatments and days lost from work and school.

Thus, infections with more than 200 different serotypes of picornavirus cause significant morbidity and mortality. The vast serotypic diversity of these viruses precludes development of vaccines for the control of human infection by these virus groups except for poliovirus and hepatitis A virus. Currently, there is no specific antiviral therapy to treat or prevent picornavirus infections.

Rotaviruses are the single most important etiologic agents of severe diarrheal illness of infant and young children world-wide. Although diarrheal diseases are one of the most common illness of infant and young children throughout the world, they assume a special significance in less developed countries, where they constitute a major cauase of mortality among the young. Rotavirus infection produces a spectrum of responses that vary from subclinical infection to mild diarrhea to a severe and occasionally fatal dehydrating illness. At present, neither a vaccine nor specific antiviral medication has been discovered for human rotavirus infections.

We have found that a group of 1,4-dihydro-4-oxoquinoline derivatives have a potent antiviral activity against picornaviruses and rotaviruses.

SUMMARY OF THE INVENTION

The present invention provides a 1,2-disubstituted 1,4-dihydro-4-oxoquinoline compound of Formula I:

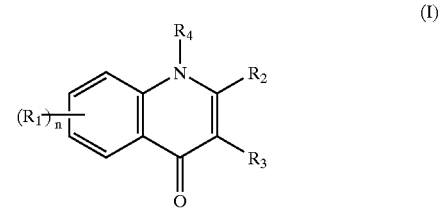

(I)

wherein each $R_1$ is a member independently selected from the group consisting of alkyl, cycloalkyl, phenyl, alkoxy, cycloalkyloxy, phenoxy, methylenedioxy, trifluoromethyl, halogen, OH, $NO_2$, $NH_2$, mono- or dialkylamino, pyrrolidino, piperidino, piperazino, 4-hydroxypiperazino, 4-methylpiperazino, 4-acetylpiperazino, morpholino, pyridyl, pyridyloxy, pyrrolyl, pyrazolyl, imidazolyl, triazolyl, thiomorpholino, dialkylaminoalkylamino, N-alkylaminoalkyl-N-alkylamino, N-hydroxyalkyl-N-alkylamino, dialkylaminoalkoxy, acetoxy, hydroxycarbonyloxy, alkoxycarbonyloxy, hydroxycarbonylmethoxy and alkoxycarbonylmethoxy, and n is 1,2 or 3;

wherein $R_2$ is a member selected from the group consisting of alkyl, pyridyl, pyrazinyl, furyl, N-alkylpyrrolyl, thiazolyl, thienyl which may be optionally substituted with alkyl or halogen, and phenyl which may be optionally substituted with up to two substituents independently selected from the group consisting of halogen, OH, alkyl, alkoxy, trifluoromethyl and acetoxy;

wherein $R_3$ is a member selected from the group consisting of hydrogen, alkyl, phenyl, alkoxy, alkoxycarbonyl, alkylsulfonyl, CN and acetyl; or if $R_2$ is a phenyl group optionally substituted with halo, alkyl or alkoxy groups, $R_3$ may represent a bridging group between the 3rd position of the quinoline ring and said phenyl group at a position next to the ring carbon atom at which said phenyl group is directly connected to the quinoline ring, said bridging group being selected from the group consisting of methylene, carbonyl, hydroxyiminomethylidene, alkoxyiminomethylidene, alkanoylaminomethylidene, aminomethylidene, hydroxymethylidene, 1-hydroxy-1,1-alkylidene, α-hydroxybenzylidene, 1-alkoxy-1,1-alkylidene, α-alkoxybenzylidene, 1,2-ethylidene and 1,3-propylidene; or if $R_2$ is 2-thienyl, 4- or 5-alkyl-2-thienyl or N-alkylpyrrol-3-yl, $R_3$ may represent methylene bridge between the 3rd position of the quinoline ring and said thienyl group at the 3rd position or said pyrrolyl group at the 2nd position, and wherein $R_4$ is a member selected from the group consisting of alkyl, alkenyl, benzyl and phenyl optionally substituted with halo, alkyl or alkoxy.

In a preferred embodiment, the compound of the present invention has Formula I-a:

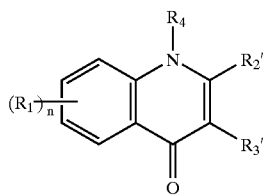

(I-a)

wherein $R_2'$ is phenyl or substituted phenyl having up to two substituents independly selected from the group consisting of halo, OH, alkyl, alkoxy, trifluoromethyl and acetoxy;

$R_3'$ is hydrogen, alkyl, phenyl, alkoxy, alkoxycarbonyl, alkyl-sulfonyl, CN or acetyl; and $R_1$, $R_4$ and n are as defined above.

In another embodiment, the compound of the present invention has Formula I-b:

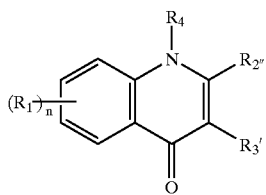

(I-b)

wherein $R_2''$ is alkyl, pyridyl, pyrazinyl, furyl, N-alkylpyrrolyl, thienyl, substituted thienyl having up to two halo- or alkyl substituents, or thiazolyl; and $R_1$, $R_3'$, $R_4$ and n are as defined above.

In other embodiments, if $R_2$ is pheny or substituted phenyl in the formula I, $R_3$ may be a bridge forming a fused ring system including the quinoline and benzene rings.

When the bridge is formed of a single carbon atom, the compound of the present invention is a derivative of 5,6-dihydro-11H-indeno[1,2-b]quinoline of Formula I-c:

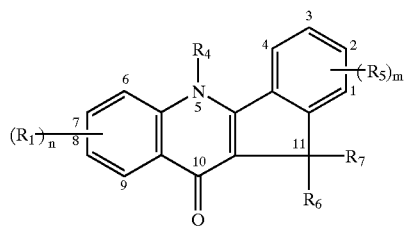

(I-c)

wherein $R_5$ is a member independly selected from the group consisting of hydrogen, halo, alkyl and alkoxy;

$R_6$ and $R_7$ together with the carbon atom to which they are attached represent a bridge selected from the group consisting of methylene, carbonyl, hydroxyiminomethylidene, alkoxyiminomethylidene, alkanoylaminomethylidene, aminomethylidene, hydroxymethylidene, 1-hydroxy-1,1-alkylidene, α-hydroxybenzylidene, 1-alkoxy-1,1-alkylidene and α-alkoxybenzylidene;

m is 1 or 2; and $R_1$, $R_4$ and n are as defined above.

When the bridge is 1,2-ethylidene, the compound of the present invention is a derivative of 6,12-dihydrobenzo[c]-acridine of Formula I-d;

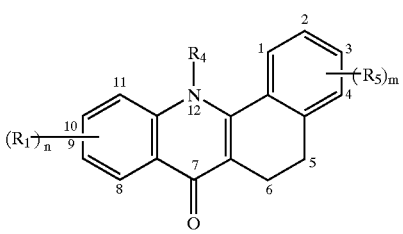

(I-d)

wherein $R_1$, $R_4$, $R_5$, n and m are as defined above.

When the bridge is 1,3-propylidene, the compound of the present invention is a derivative of 5,6,7,13-tetrahydro-8H-benzo[6,7]cyclohepta[1,2-b]quinoline of Formula I-e;

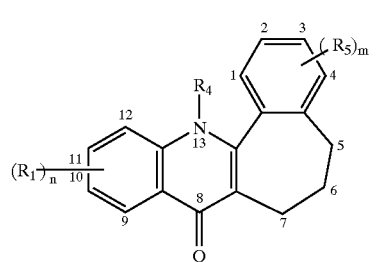

(I-e)

wherein $R_1$, $R_4$, $R_5$, n and m are as defined above.

In further embodiments, if $R_2$ is thienyl, 4- or 5-alkyl-2-thienyl or N-alkyl-pyrrol-3-yl, $R_3$ may be a methylene bridge forming a fused ring system including the quinoline ring and the thiophene or pyrrole ring. Thus, the compounds of the present invention include a derivative of thieno[3', 2':4,5]-cyclopenta[1,2-b]quinoline-5-one of Formula I-f:

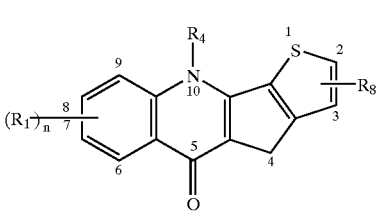

(I-f)

wherein $R_8$ is hydrogen or alkyl; and $R_3$, $R_4$ and n are as defined above.

Also included in the compounds of the present invention is a derivative of pyrrolo[3',2':4,5]cyclopenta[1,2-b] quinoline-5-one of Formula I-g:

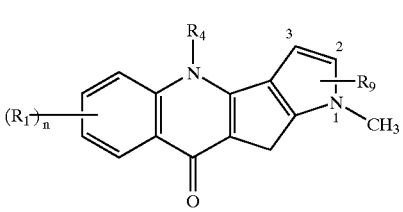

(I-g)

wherein $R_9$ is alkyl, and $R_1$, $R_4$ and n are as define.

The compounds of the present invention also include a pharmaceutically acceptable acid addition salt or quaternary ammonium salt thereof.

The invention also relates to a pharmaceutical composition comprising a compound of Formula I above and a pharmaceutically acceptable carrier. The pharmaceutical composition of the invention is useful in the prophylaxis and the treatment of viral infections of Picornavirus and human rotavirus.

DETAILED DESCRIPTION OF THE INVENTION

Throughout the specification and claims, several terms are difined as follows.

Alkyl including the alkyl moiety of alkoxy refers to a straight chain or branched alkyl of up to 8, preferably 6 carbon atoms.

Alkenyl refers to an alkenyl of 2–6, preferably 3–4 carbon atoms.

Cycloalkyl refers to a cycloalkyl of 5–7 carbon atoms, preferably cyclohexyl.

Halogen refers to fluorine, chlorine or bromine.

The compounds of Formula I may be synthesized by use of known chemical reactions and procedures starting from appropriately substituted aniline II.

Generally, the synthesis of the compounds of Formula I follows either Method A or Method B. In Method A, substituted anilines II are reacted with 2-benzoylalkanoic acid ethyl ester III in the presence of polyphosphoric acid to give 2-phenyl-4-oxoquinoline derivatives (IV) followed by the reaction with $R_4I$ in the presence of sodium hydride. Method A is applicable to the synthesis of the compounds of Formula I-a.

Scheme I

Method A

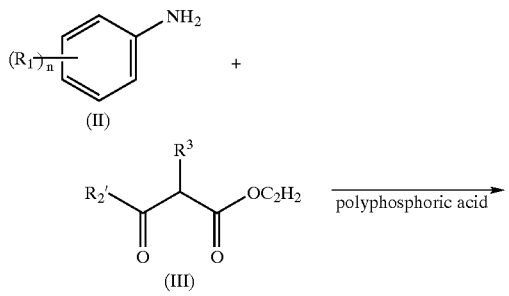

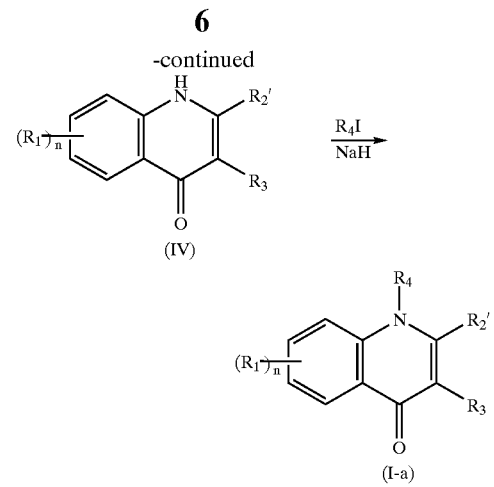

In Method B, the compounds of formula I are prepared from substituted anilines II via N-substituted isatoic anhydrides VIII.

The intermediate VIII, in turn, may be synthesized by two methods as shown in Scheme II below. Substituted anilines II are reacted with chloral hydrate and hydroxylamine to yield nitrosoacetanilide V. Cyclization of V into substituted isatins VI followed by introduction of $R_4$ at position 1 yields N-substituted isatins VII. N-substituted isatoic anhydrides VIII are obtained by treating VII with m-chloroperbenzoic acid(m-CPBA). Alternatively, N-substituted isatoic anhydride VIII may be prepared by reacting isatins VI with m-CPBA to produce N-unsubstituted isatoic anhydrides IX followed by introduction of $R_4$ at position 1. N-substituted isatins VII may also be prepared by reacting N-substituted anilines XII with oxalyl chloride followed by aluminum chloride. N-substituted anilines XII, in turn, may be prepared by acetylating substituted anilines II, reacting the resulting acetanilides X with an alkylating agent to introduce $R_4$ followed by deacetylation of the N-substituted acetanilides XI.

Scheme II Synthesis of N-substituted Isatoic Anhydrides

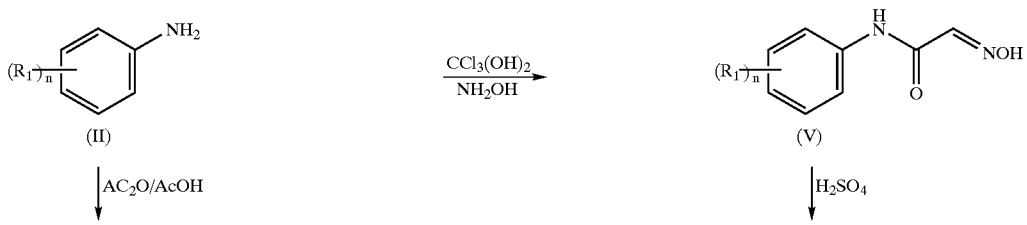

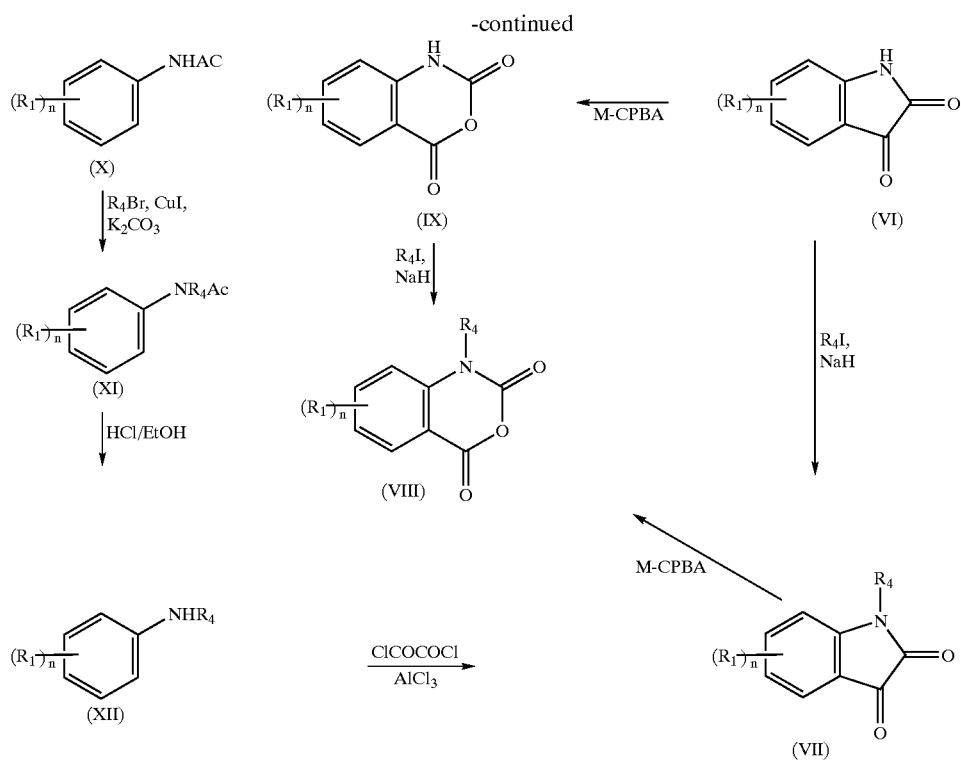

N-Substituted isatoic anhydrides VIII are used in Method B for the synthesis of the compounds of Formula I by the reaction with an appropriate ketone in the presence of n-butyl lithium and tetramethylethylenediamine (TMEDA) or in the presence of sodium hydride.

In Method B1 for the preparation of the compounds of Formula I-a, the ketone compound may be represented by the formula: $R_2'C(O)CH_2R_3'$, wherein $R_2'$ is phenyl or substituted phenyl having one or two substituents independently selected from the group consisting of halo, OH, alkyl, alkoxy, trifluoromethyl and acetoxy; and $R_3'$ is hydrogen, alkyl, phenyl, alkoxy, alkoxycarbonyl, alkylsulfonyl, CN or acetyl. The reaction involved in Method B1 is shown in Scheme III.

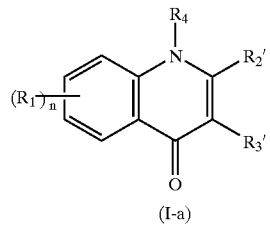

(I-a)

Similarly, Method B2 for the preparation of the compounds I-b, a ketone of the formula: $R_2''C(O)CH_2R_3'$, wherein $R_2''$ is alkyl, pyridyl, pyrazinyl, furyl, N-alkylpyrrolyl, thienyl, substituted thienyl having up to two halo- or alkyl substituent or thiazolyl; and $R_3'$ is as defined above is used. The reaction involved in Method B2 is shown in Scheme IV.

Scheme III

Method B1

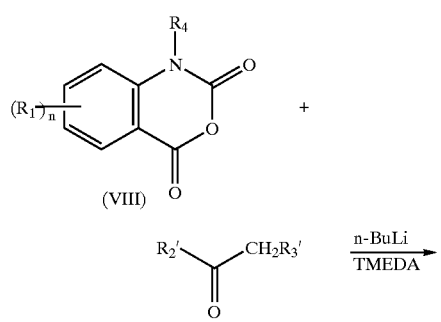

Scheme IV

Method B2

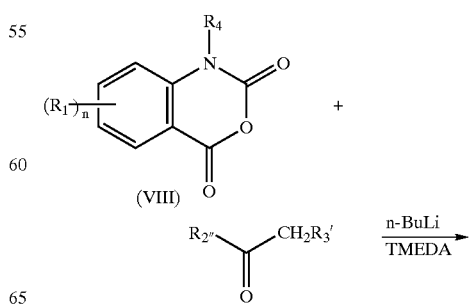

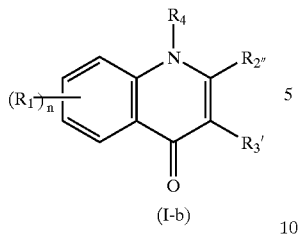

(I-b)

The compounds of Formula I-c wherein both $R_6$ and $R_7$ are hydrogen as well as the compounds of Formula I-d and Formula I-e are prepared by Method B3 shown in Scheme V.

Scheme V

Method B3

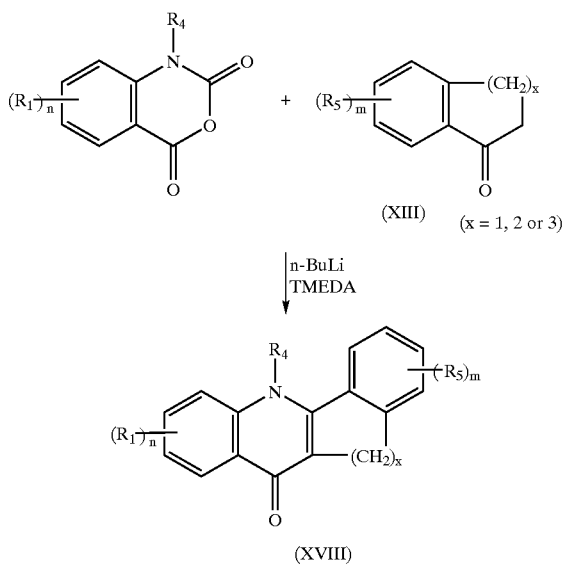

(x = 1, 2 or 3)

Specifically, the oxo compound XIII are 1-indanones for the compounds of Formula I-c(x=1, $R_6$, $R_7$=H), 1-tetralones for the compounds Formula I-d (x=2) and 1-oxobenzosuberones (x=3), respectively.

The compounds of Formula I-c wherein $R_6$ and $R_7$ together represent oxo may be prepared by reacting the isatoic anhydride VIII with a 1,3-indandione XIV to obtain 5,10-dihydro-11H-indeno[1,2-b]quinolin-10,11-dione compounds XV as shown in Scheme VI.

Scheme VI Reaction of isatoic anhydride with 1,3-indanedione

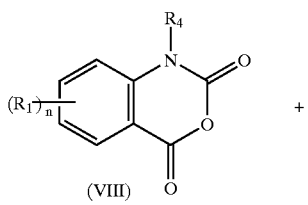

(VIII)

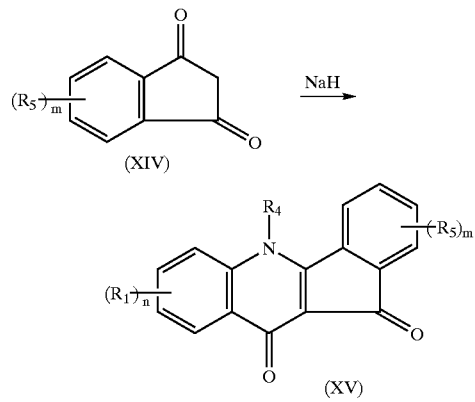

The 11-oxo compounds XV may be further manipulated using known methodoloy to obtain the compounds of Formula I-c wherein $R_6$ and $R_7$ are other than oxo. Reaction of 11-oxo compounds XV with hydroxylamine gives a corresponding oxime. Reaction of oxime with an alkylating agent in the presence of sodium hydride gives a 11-alkoxyimino compound. The oxime further gives a 11-alkanoylamino compound by acylation with an acylating agent such as acetyl anhydride in a reducing atmosphere. Saponification of 11-alkanoylamino compound leads to 11-amino compound.

The 11-oxo compounds XV may be converted into a 11-hydroxy compound by the reaction with sodium borohydride. Reaction of 11-oxo compounds XV with alkyl- or phenyl magnesium halide leads to a 11-hydroxy-11-alkyl or phenyl devivative. The hydroxy group at position 11 may further be alkylated in the presence of sodium hydride to give a 11-alkoxy-11-alkyl or phenyl derivative. The hydroxy group at position 11 may be removed by the reaction with sodium iodide and trimethylsilyl chloride to give 11-alkyl or phenyl derivative.

Finally, the compounds of Formula I-f and Formula I-g may be prepared by Method B4 as shown in Scheme VII. The compounds of Formula I-f are prepared by the reaction of isatoic anhydride VIII with 4,5-dihydro-6H-cyclopenta[b]-thiophen-6-one XVI in the presence of n-BuLi and TMEDA. Reaction of isatoic anhydride VIII with 1-methyl-5,6-dihydro-4H-cyclopenta[b]pyrrol-4-one XVII in the presence of n-BuLi and TMEDA gives the compounds of Formula I-g.

Scheme VII

Method B4

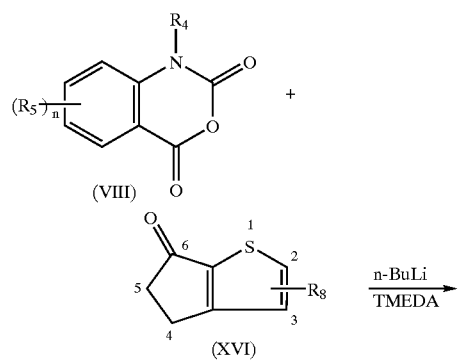

-continued

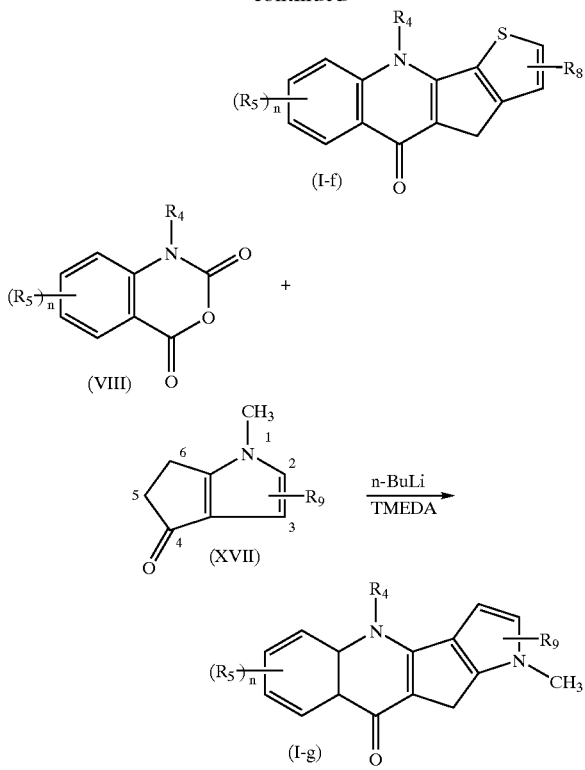

EXAMPLES

The following examples are given for illustrative purposes only.

Part A.

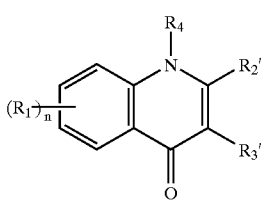

Example 1

1-Ethyl-2-phenyl-3-methyl-6-isopropyl-1,4-dihydro-4-oxoquinoline(Compound A37).

Step 1. 2-phenyl-3-methyl-6-isopropyl-1,4-dihydro-4-oxoquinoline

To polyphosphoric acid (1.5 g) heated to 160° C. were added dropwise a solution of 4-isopropylaniline(0.5 g, 3.6 mmol) and ethyl 2-benzoylpropionate (1.52 g, 7.3 mmol) in ethanol with stirring. The mixture was stirred at 160° C. for 3 hours. After cooling, a cold solution of 10% hydrochloric acid was added to the mixture. The resulting precipitate was recovered by filtration, dissolved in methanol and treated with active carbon. After evaporating in vacuo, the residue was recrystallized from ethyl acetate to give the title compound in a yield of 81%. $^1$H-NMR(DMSO-$d_6$)δ 1.28(6H,d, CH(CH$_3$)$_2$), 2.0(3H,s,CH$_3$), 3.07(1H,septet,CH), 7.61(5H,s, Ar-H), 7.6–7.7(2H,m,H-7,8), 8.13(1H,s,H-5), 12.67(1H,s, NH)

Step 2. 1-ethyl-2-phenyl-3-methyl-6-isopropyl-1,4-dihydro-4-oxoquinoline

To a solution of 0.28 g(1 mmol) of 2-phenyl-3-methyl-6-isopropyl-1,4-dihydro-4-oxoquiline in DMF(10 mL) were added potassium carbonate(3 mmol) and ethyl iodide(5 mmol). The mixture was heated with stirring for 4.5 hours. After removing the solvent, the residue was dissolved in water and extracted with ethyl acetate twice. The combined organic layers were washed with water and then saturated sodium chloride solution followed by drying with sodium sulfate and evaporation in vacuo. The residue was purified by silica gel- column chromatography(hexane:ethyl acetate= 2:1) to yield the title compound. $^1$H-NMR(CDCl$_3$)δ 1.1–1.4 (3H,t,NCH$_2$CH$_3$), 1.3–1.5(6H,d,CH(CH$_3$)$_2$), 1.8(3H,s,CH$_3$), 2.7–3.4(1H,m,CH), 3.8–4.2(2H,q,NCH$_2$), 7.1–7.8(7H, m,Ar-H), 8.3–8.6(1H,s,H-5).

Example 2

1-Ethyl-2-(3-methyl-4-methoxyphenyl)-3,5-dimethyl-6-isobutoxy-1,4-dihydro-4-oxoquinoline (Compound A191)

Step 1. 3'-Methyl-4'-methoxyacetophenone

To an ice-cooled solution of 3'-methyl-4'-hydroxyacetophenone (15 g, 100 mmol) in 100 mL of DMF was added 60% sodium hydride (2.4 g, 101 mmol) under argon atmosphere with stirring. After 30 minutes, methyl iodide(7.5 mL, 120 mmol) was added to the solution and allowed to react overnight at room temperature with stirring. The reaction mixture was evaporated to remove the solvent. The residue was dissolved in water and extracted with diethyl ether thrice. The combined organic layers were sequentially washed with water and saturated sodium chloride solution, dried with sodium sulfate and distilled under reduced pressure (116° C./0.2 mmHg) to obain the title compound in a yield of 71%. $^1$H-NMR(CDCl$_3$) δ 2.24(3H, s,CH$_3$), 2.54(3H,s,COCH$_3$), 3.90(3H,s,OCH$_3$), 6.84(1H,d, H-5'), 7.77(1H,dd,H-2'), 7.82(1H,dd,H-6')

Step 2. 3-Methyl-4-methoxybenzoic acid

To a suspension of bleaching powder(72 g, 500 mmol) in 270 mL of water was added a solution of potassium hydroxide (14 g, 250 mmol) and potassium carbonate (50.5 g 365 mmol) in 150 mL of water. The suspension was stirred for 2 hours under sealing and the filtered to remove precipitated calcium salt. The precipitate was washed with a small amount of water and washing was combined with the above filtrate. To the filtrate was added 3'-methyl-4'-methoxyacetophenone (27.3 g, 166 mmol) while stirring vigorously. The mixture was stirred overnight at room temperature. After adding sodium bisulfate (17.8 g 171 mmol), the reaction mixture was washed twice with diethyl ether. The aqueous layer was acidified with hydrochloric acid. The resulting crystals were filtered off followed by drying under reduce pressure to yield the title compound.

$^1$-H-NMR(CDCl$_3$) δ 2,18(3H,s,CH$_3$), 3.89(3H,s,OCH$_3$), 7.02(1H,d,H-5), 7.74(1H,dd,H-2), 7.81(1H,dd,H-6)

Step 3. Ethyl 3-methyl-4-methoxybenzoate

A solution of 3-methyl-4-methoxybenzoic acid (20 g, 120 mmol) and ethyl orthoformate (19.6 g 132 mmol) in 300 mL of ethanol was refluxed overnight with the addition of concentrated sulfuric acid (4 mL) followed by evaporation in vacuo to remove the solvent. The residue was dissolved in water. The solution was made alkaline with sodium carbonate and extracted thrice with chloroform. The combined organic layers were sequentially washed with saturated sodium carbonate solution, water and saturated sodium chloride solution, dried with sodium sulfate and distilled under reduced pressure (185–190° C./0.3 mmHg) to give the title compound. $^1$H-NMR(CDCl$_3$) δ 1,38(3H,t,CH$_2$CH$_3$), 2.23(3H,s,3-CH$_3$), 3.87(3H,s,OCH$_3$), 4.34(2H,dq,CH$_2$CH$_3$), 6.82(1H,d,H-5), 7.83(1H,dd,H-2), 7.89(1H,dd,H-6)

Step 4. Ethyl 2-(3-methyl-4-methoxybenzoyl)propionate

To a mixture of ethyl 3-methyl-4-methoxybenzoate (24.8 g 128 mmol) and 60% sodium hydride (3.1 g, 128 mmol) under argon atmosphere was added dropwise a solution of ethyl propionate (6.5 g, 64 mmol) in 200 mL of n-butyl ether with stirring while keeping the inner temperature at 90–100° C. Stirring was continued for additional 3 hours at 130° C. After cooling to room temperature, excessive sodium hydride in the reaction mixture was decomposed with ethanol. After the addition of water, the reaction mixture was neutrallized with hydrochloric acid and extracted with diethyl ether thrice. The combined organic layers were sequentially washed with saturated sodium carbonate solution, water and saturated sodium chloride solution followed by drying with sodium sulfate. Distillation of the organic layers under reduced pressure (185–190° C./0.3 mmHg) gave the title compound. $^1$H-NMR(CDCl$_3$)δ 1.19 (3H,t,CH$_2$CH$_3$), 1.47(3H,d,CHCH$_3$), 2,25(3H,s,3'-CH$_3$), 3.90(3H,s,OCH$_3$), 4.15(2H,dq,CH$_2$CH$_3$), 4.34(1H,q,CH), 6.86(1H,d,H-5'), 7.80(1H,dd,H-2'), 7.86(1H,dd,H-6')

Step 5. 3-Methyl-4-isobutoxynitrobenzene

Isobutyl alcohol (1.5 g, 5 mmol) was dissolved in anhydrous DMF under argon atmosphere and cooled to −15° C. To this solution was added 60% sodium hydride (0.37 g, 15.5 mmol) with stirring followed by 2-nitro-5-fluorotoluene (2 g, 13 mmol) after 30 minutes. The mixture was stirred for additional 2 hours at the same temperature followed by distilling off DMF. The residue was diluted with water and extracted with chloroform thrice. The combined organic layers was sequentially washed with water and saturated sodium chloride solution, dried with sodium sulfate and purified by silica gel-column chromatography (chloroform) to give the titel compound. $^1$H-NMR(CDCl$_3$)δ 1.07(6H,d,(CH$_3$)$_2$), 2.16(1H,septet,CH), 2.29(3H,s,3-CH$_3$), 3.83(2H,d,CH$_2$), 6.82(1H,d,H-5), 8.04(1H,d,H-2), 8.08(1H,dd,H-6)

Step 6. 3-methyl-4-isobutoxyaniline

To a solution of 3-methyl-4-isobutoxynitrobenzene (2.72 g, 13 mmol) in ethanol (25 mL) were added iron powder (13 g), water (1.5 mL) and concentrated hydrochloric acid (0.13 mL). The mixture was refluxed for 1 hour and then filtered while hot. The filtrate was concentrated in vacuo. The residue was dissolved in chloroform followed by drying with sodium sulfate. Removal of chloroform by evaporation gave the title compound. $^1$H-NMR(CDCl$_3$) δ 1.01(6H,d,CH(CH$_3$)$_2$), 2.06(1H,septet,CH), 2.17(3H,s,3-CH$_3$), 3.33(2H,brs,NH$_2$), 3.63(2H,d,CH$_2$), 6.53(1H,d,H-2), 6.63(1H,d,H-5), 6.67(1H,dd,H-6)

Step 7. 2-(3-Methyl-4-methoxyphenyl)-3,5-dimethyl-6-isobutoxy-1,4-dihydro-4-oxoquinoline To polyphosphoric acid (3 g) heated to 160° C. was added dropwise a solution of ethyl 2-(3-methyl-4-methoxybenzoyl) propionate (3,4 g,13.4 mmol) and 3-methyl-4-isobutoxyaniline (1.2 g, 6.7 mmol) in ethanol (2 mL) with stirring.

The mixture was stirred for additional 1 hour and allowed to cool to room temperature. An amount of crashed ice and 20% hydrochloric acid were added to the reaction mixture and extracted with chloroform. The organic layer was washed sequentially with saturated sodoium carbonate solution, water and saturated sodium chloride solution followed by drying with sodium sulfate. The residue resulting from evaporation of chloroform was roughly purified by silica gel-column chromatography(chloroform: acetone= 20:1).

The title compound was obtained by crystallizing the crude product from diethyl ether. $^1$H-NMR(CDCl$_3$) δ 1.08 (6H,d,CH(CH$_3$)$_2$), 1.87(3H,s,3-CH$_3$), 2.07(3H,s,3'-CH$_3$), 2,14(1H,septet,CH), 2.91(3H,s,5-CH$_3$), 3.75(2H,d,CH$_2$), 3.76(3H,s,OCH$_3$), 6.65(1H,s,H-5'), 7.11(1H,d,H-2'), 7.13 (1H,dd,H-6'), 7.21(1H,d,H-8), 7.48(1H,d,H-7), 9.78(1H,s, NH)

Step 8. 1-Ethyl-2-(3-methyl-4-methoxyphenyl)-3,5-dimethyl-6-isobutoxy-1,4-dihydro-4-oxoquinoline 2-(3-Methyl-4-methoxyphenyl)-3,5-dimethyl-6-isobutoxy-1,4-dihydro-4-oxoquinoline(0.18 g, 0.5 mmol) was dissolved in anhydrous DMF under argon atmosphere.

To the solution were added while ice cooling and stirring 60% sodium hydride (0.013 g, 0.54 mmol). After 30 minutes, ethyl iodide (0.12 g, 0.75 mmol) was added to the mixture followed by stirring overnight. After removing DMF by distillation, water was added to the reaction mixture followed by extraction with ethyl acetate thrice. The combined organic layers were washed sequentially with water and saturated sodium chloride solution, dried with sodium sulfate and then concentrated in vacuo. The residue was purified by silica gel-column chromatography (n-hexane:ethyl acetate=3:1) to give the title compound. $^1$H-NMR(CDCl$_3$) δ 1.08(6H,d,CH(CH$_3$)$_2$), 1.19(3H,t,CH$_2$CH$_3$), 1.77(3H,s,3-CH$_3$), 2.15(1H,septet,CH), 2.28(3H,s,3'-CH$_3$), 2.98(3H,s,5-CH$_3$), 3.78(2H,d,OCH$_2$), 3.91(3H,s,OCH$_3$), 3.96(3H,q,CH$_2$CH$_3$), 6.93(1H,d,H-5'), 7.03(1H,d,H-2'), 7.05(1H,dd,H-6'), 7.25(1H,d,H-8), 7.33(1H,d,H-7)

Example 3

1-(4-chlorophenyl)-2-phenyl-3-methyl-6-isopropyl-1,4-dihydro-4-oxoquinoline(Compound A324)

Step 1. 4-Isopropylacetanilide

To a solution of 4-isopropylaniline (5.2 g, 38 mmol) in acetic acid was added while ice-cooling and stirring acetic anhydride (4 ml, 42 mmol). After stirring at room temperature overnight, the reaction mixture was poured into ice water. The resulting precipitate was filtered off, washed with water and then dried under reduced pressure to give the title compound. LH-NMR(CDCl$_3$) δ 1.22(6H,d,CH(CH$_3$)$_2$), 2.15 (3H,s,NHCOCH$_3$), 2.87(1H,septet,CH), 7.28(4H,d,Ar-H)

Step 2. 1-(4-Chlorophenyl)-4-isopropylacetanilide

Under argon atmosphere, a mixture of 4-isopropyl-acetanilide (2.5 g, 5 mmol), 4-chlorobromobenzene (2.97 g, 15.5 mmol), cupric iodide (2.95 g, 15.5 mmol) and potassium carbonate (1.5 g, 10.9 mmol) was heated at 160–180° C. for 30 hours followed by allowing to cool. The reaction mixture was diluted with water and diethyl ether and filtered to remove insolubles. The organic layer was separated, washed with water and saturated sodium chloride solution and dried with sodium sulfate. After removing the solvent, the residue was purified by silica gel-column chromatography (chloroform) to yield the title compound. $^1$-HNMR(CDCl$_3$)δ 1.25(6H,d,CH(CH$_3$)$_2$), 2.05(3H,s, NCOCH$_3$), 2.92(4H,septet,CH), 7.15–7.28(8H,m,Ar-H)

Step 3. 1-(4-Chlorophenyl)-4-isopropylaniline

A solution of 1-(4-chlorophenyl)-4-isopropylacetanilide (2.91 g, 10 mmol) in ethanol (35 mL) was mixed with 15 mL of concentrated hydrochloric acid. The mixture was refluxed overnight and evaporated to remove ethanol. The resulting residue was diluted with water and made alkaline with sodium hydroxide. This solution was extracted with diethyl ether twice. The combined organic layers were sequentially washed with water and saturated sodium chloride solution, dried with sodium sulfate and evaporated in vacuo to give the title compound. $^1$H-NMR(CDCl$_3$)δ 1.24(6H,d,CH(CH$_3$)$_2$), 2.87(1H,septet,CH), 5,59(1H,s,NH), 6.91–7.19(8H, m,Ar-H)

Step 4. 1-(4-Chlorophenyl)-5-isopropylisatin

To a solution of 1-(4-chlorophenyl)-4-isopropylaniline (2.29 g, 9.3 mmol) in dry benzene under argon atmosphere was added oxalyl chloride (1.42 mL, 16.3 mmol) while ice cooling and stirring. The mixture was stirred at room temperature for additional 2 hours followed by evaporation under reduced pressure to remove excessive oxalyl chloride. The residue was dissolved in 1,2-dichloroethane. To this solution was added under argon atmosphere anhydrous aluminum chloride (1.28 g, 9.6 mmol) in portions. The mixture was stirred at room temperature overnight and then gradually poured into ice-water (40 mL) containing 10 mL of 2N hydrochloric acid solution. The organic phase was separated, sequentially washed with 2N sodium hydrogen carbonate solution, water and saturated sodium chloride solution, dried with sodium sulfate and evaporated under reduced pressure to remove 1,2-dichloroethane. The title compound was obtained by crystalizing the residue from diethyl ether, $^1$H-NMR(CDCl$_3$)δ 1.24(6H,d,CH(CH$_3$)$_2$, 2,92 (1H,septet,CH), 6.82(1H,d,H-7), 7.36–7.55(4H,m,Ar-H), 7.42(1H,dd,H-6), 7.59(1H,d,H-4)

Step 5. 1-(4-Chlorophenyl)-6-isopropylisatoic anhydride

A solution of 1-(4-chlorophenyl)-5-isopropylisatin (1.5 g, 5.0 mmol) in methylene chloride was added dropwise to a solution of m-chloroperbenzoic acid (907 mg, 5.3 mmol) in methylene chloride. The mixture was stirred at room temperature for 2 hours and then poured into ice-water containing 3 equivalents of sodium hydrogen sulfite followed by extraction with methylene chloride. The methylene chloride layer was sequentially washed with 1% sodium hydrogen carbonate solution, water and saturated sodium chloride solution, dried with sodium sulfate and then evaporated to remove methylene chloride. The title compound was obtained by crystallizing the residue from diethyl ether. $^1$H-NMR(CDCl$_3$)δ 1.24(6H,d,CH(CH$_3$)$_2$), 2.95(1H,septet,CH), 6.49(1H,d,H-8), 6.98(1H,dd,H-7), 7.26–7.60(4H,m,Ar-H), 8.03(1H,d,H-5)

Step 6. 1-(4-Chlorphenyl)-2-phenyl-3-methyl-6-isopropyl-1,4-dihydro-4-oxoquinoline Tetramethylethylenediamine(1.05 mL, 6.94 mmol) was gradially added with stirring into a solution of 1.55M hexane solution of n-butyl lithium (4.5 mL, 6.94 mmol) under argon atmosphere. Then a solution of propiophenone(936 mg, 6.94 mmol) in anhydrous THF was aded to the mixture while ice cooling and stirring. The reaction mixture was stirred for additional 3 hours at room temperatured and then ice-cooled.

To this was added dropwise a solution of 1-(4-chlorophenyl)-6-isopropylisatoic anhydride (1.10 g, 3.47 mmol) in anhydrous THF. The reaction mixture was stirred overnight at room temperature and diluted with saturated ammonium chloride. The organic layer was separated and concentrated in vacuo. The residue was dissolved in ethyl acetate. The resulting solution was washed with saturated sodium chloride solution, dried with sodium sulfate and evaporated to remove the solvent. The residue was purified by silica gel-column chromatography (chloroform:acetone=20: 1) followed by crystallization from diethyl ether to give the title compound. $^1$-H-NMR(CDCl$_3$)δ 1.31(6H,d,CH(CH$_3$)$_2$), 1.91(3H,s,CH$_3$), 3.05(1H,septet,CH), 6.67(1H,d,H-8), 7.01–7.28(9H,m,Ar-H), 7.33(1H,dd,H-7), 8.39(1H,d,H-5)

Example 4

1,2-Diphenyl-3-methyl-6-isopropyl-1,4-dihydro-4-oxoquinoline (Compound A320)

Step 1. 4-Isopropylisonitrosoacetanilide

A solution of chloral hydrate (9.0 g, 54 mmol) and anhydrous sodium sulfate (57 g) in 190 mL of water was heated to 60° C. To this solution were added a warmed solution (70° C.) of 4-isopropylaniline (6.8 g, 50 mmol) and concentrated hydrochloric acid (4.3 mL, 52 mmol) in 150 mL of water followed by a warmed solution of hydroxylamine hydrochloride (11.0 g, 158 mmol) in 50 mL of water. The resulting solution was heated to boiling temperature over 40 minutes and then refluxed for 2 minutes. After cooling with tap water, the resulting precipitate was filtered off, washed with cold water and dried under reduced pressure to give the title compound. $^1$H-NMR(CDCl$_3$) δ 1.21 (6H,d,CH$_3$), 2.96(1H,septet,CH), 6.72(1H,brs,OH), 7.18 (2H,d,H-3.5), 7.47(2H,d,H-2,6), 7.58(1H,s,CH=N), 8.34 (1H,s,NH)

Step 2. 5-Isopropylisatin 30 mL of concentrated sulfuric acid was heated to 50° C. To this was added 4-isopropylnitrosoacetanilide (8.4 g, 41 mmol) in portions while maintaing the inner temperature at 60–70° C. The reaction mixture was heated at 80° C. for 10 minutes with stirring, allowed to cool to room temperature and poured into ice(about 300 g). The resulting precipitate was filtered off, washed with cold water and dried under reduced pressure to give the title compound. $^1$-H-NMR (CDCl$_3$) δ 1.21(6H,d,CH$_3$), 2.96(1H,septet,CH), 7.10(1H,d, H-8), 7.67(1H,d,H-7), 7.74(1H,d,H-5), 11.66(1H,brs,NH)

Step 3. 1-Phenyl-5-isopropylisatin

A solution of 5-isopropylisatin (500 mg, 2.6 mmol), bromobenzene(10 mmol) and cupric iodide (420 mg, 5.3 mmol) in DMF was heated at 180° C. for 5.5 hours with stirring. The reaction mixture was filtered while hot and the filtrate was concentrated in vacuo. The residue was dissolved in chloroform followed by drying with sodium sulfate. The chloroform solution was evaporated to remove the solvent and the residue was purified by silica gel-chromatography (chloroform) to give the title compound. $^1$H-NMR(CDCl$_3$) δ 1.25(6H,d,CH(CH$_3$)$_2$, 2.92(1H,septet, CH), 6.83(1H,d,H-7), 7.38–7.57(6H,m,Ar-H), 7.59(1H,d,H-4)

Steps 4 and 5. 1,2-Diphenyl-3-methyl-6-isopropyl-1,4-dihydro-4-oxoquinoline

The title compound was prepared from 1-phenyl-5-isopropylisatin in a manner analogous to steps 5 and 6 of Example 3

1H-NMR(CDCl$_3$) δ 1.31(6H,d,CH(CH$_3$)$_2$), 1.93(3H,s, CH$_3$), 3.05(1H,septet,CH), 6.69(1H,d,H-8), 7.04–7.33(11H, m,Ar-H)

Example 5

1-Methyl-2-phenyl-3-ethoxycarbonyl-6-isopropyl-1,4-dihydro-4-oxoquinoline (Compound A50)

Step 1. 6-Isopropylisatoic anhydride

To a solution of m-chloroperbenzoic acid (5 g, 28.5 mmol) in THF (20 mL) was added dropwise a solution of 5-isopropylisatin (2.7 g, 14.3 mmol) in THF (50 mL) under ice-cooling and stirring. After stirring for additional 3 hours under ice-cooling, the reaction mixture was treated with 10% sodium hydrogen sulfite solution (60 mL) to decompose excessive m-CPBA. The solution was poured into ice water (200 mL) and extracted with ethyl acetate several times. The combined organic layers were washed with water and saturated sodium chloride solution, dried with sodium sulfate and concentrated in vacuo. The resulting residue was crystallized from diethyl ether to give the title compound. $^1$H-NMR(CDCl$_3$) δ 1.23(6H,d,CH(CH$_3$)$_2$), 2.88(1H,septet,CH), 6.95(1H,d,H-7), 7.43(1H,dd,H-6), 7.47(1H,d,H-4)

Step 2. 1-Methyl-6-isopropylisatoic anhydride

To a suspension of 60% sodium hydride (0.54 g, 13.4 mmol) in anhydrous DMF(30 mL), 6-isopropylisatoic anhydride (2.5 g, 12.2 mmol) was added at room temperature under argon atmosphere with stirring. After 30 minutes, methyl iodide (1.99, 13.4 mmol) was added to the reaction mixture followed by stirring at room temperature overnight. The reaction mixture was evaporated to remove DMF and extracted with chloroform. The extract was washed with water and saturates sodoium chloride solution, dried with sodium sulfate and evaporated in vacuo to dryness. The titled compound was obtained by crystalling the residue from diethyl ether. $^1$H-NMR(CDCl$_3$) δ 1.28(6H,d,CH(CH$_3$)$_2$), 2.99(1H,septet,CH), 3.57(3H,s,N-CH$_3$), 7.12(1H,d,H-8), 7.64(1H,dd,H-7), 8.01(1H,d,H-5)

Step 3. 1-Methyl-2-phenyl-3-ethoxycarbonyl-6-isopropyl-1,4-dihydro-4-oxoquinoline To a suspension of 60% sodium hydride (0.06 g, 1.5 mmol) in anhydrous DMF (10 mL) was added ethyl benzoylacetate (0.29 g, 1,5 mmol) at room temperature under argon atmosphere with stirring. After 30 minutes, 1-metyl-6-isopropylisatoic anhydride (0.33 g, 1,5 mmol) was added to the mixture at 60° C. with stirring. The temperature was raised to 120° C. over 1 hour. The stirring was continued at the same temperature for additional 4 hours. The reaction mixture was concentrated under reduced pressure. The residue was purified by silica gel-chromatography (chloroform: acetone=9:1) followed by crystallization from diethyl ether to obtain the desired compound. $^1$H-NMR (CDCl$_3$) δ 0.93 (3H,t,CH$_2$CH$_3$), 1.35(6H,d,CH(CH$_3$)$_2$, 3.09(1H,septet,CH), 3.98(2H,q,OCH$_3$), 7.39–7.41(2H,m,H-2',6'), 7.47–7.50(4H,m,H-3',4',5',8'), 7.61(1H,dd,H-7), 8.40(1H,d,H-5)

Example 6

1-Ethyl-2-(2-furyl)-6-isopropyl-1,4-dihydro-4-oxoquinoline (Compound A304)

Step 1. 1-Ethyl-6-isopropylisatoic anhydride

6-Propylisatoic anhydride was reacted with ethyl iodide in the presence of sodium hydride in a manner analogous to step 2 of Example 5 to prepare the title compound. $^1$H-NMR (CDCl$_3$)δ 1.28(6H,d,CH(CH$_3$)$_2$), 1.38(3H,t,CH$_2$CH$_3$), 2.99 (1H,septet,CH), 4.13(2H,q,NCH$_2$), 7.14(1H,d,H-8), 7.64 (1H,dd,H-7), 8.01(1H,d,H-5)

Step 2. 1-Ethyl-2-(2-furyl)-6-isopropyl-1,4-dihydro-4-oxoquinoline

To a 1.6M solution of n-butyl lithium in hexane (1,38 mL, 2,2 mmol) was added tetramethylethylenediamine (0.3 mL, 2,2 mmol) under argon atmosphere at room temperature with stirring. Then 2-acetylfuran (242 mg, 2,2 mmol) in anhydrous THF was added dropwise to the mixture under ice cooling followed by stirring for 1 hour. To this mixture was added 1-ethyl-6-isopropylisatoic anhydride (250 mg, 1.1 mmol) in anhydrous THF. After stirring at room temperature overnight, the reaction mixture was diluted with saturated aqueous solution of ammonium chloride. The resulting organic layer was separated and concentrated under reduced pressure. The residue was dissolved in ethyl acetate and then washed with saturated sodium chloride solution followed by drying with sodium sulfate. After removing ethyl acetate by evaporation in vacuo, the residue was subjected to preparative TLC(n-hexane:ethyl acetate=2:1) to separate the title compound followed by crystallization from diethyl ether. $^1$H-NMR(CDCl$_3$) δ1.33(6H,d,CH(CH$_3$)$_2$), 1.55(3H,t,CH$_2$CH$_3$), 3.08(1H,septet,CH), 4.17(2H,q,NCH$_2$), 6.48(1H,s,H-3), 6.56–6.58(1H,m,furan H-4'), 6.76(1H,dd,furan H-5'), 7.54(1H,d,H-8), 7.59(1H,dd,H-7), 7.63(1H,dd,furan H-3'), 8.34(1H,d,H-5)

The following compounds have been produced in a manner analogous to that described in the preceding examples.

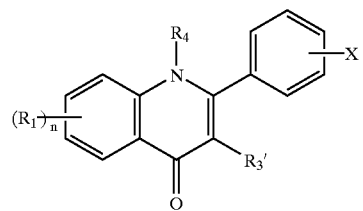

TABLE I

| Compound No. | R$_1$ | X | R$_3$' | R$_4$ | m.p.(° C.) |
|---|---|---|---|---|---|
| A12 | 6-Br | H | H | CH$_3$ | 166–168 |
| A13 | 5-OH | H | CH$_3$ | CH$_3$ | 282–283 |
| A14 | 6-OH | H | CH$_3$ | CH$_3$ | >300 |
| A15 | 7-OH | H | CH$_3$ | CH$_3$ | >300 |
| A16 | 8-OH | H | CH$_3$ | CH$_3$ | 240–242 |
| A17 | 6-CH$_3$ | H | H | C$_2$H$_5$ | 169–170 |
| A18 | 6-CH$_3$ | H | CH$_3$ | C$_2$H$_5$ | 167–170 |
| A19 | 5-CH$_3$O | H | CH$_3$ | CH$_3$ | 141–142 |
| A20 | 6-CH$_3$O | H | CH$_3$ | CH$_3$ | 154–156 |
| A21 | 6-CH$_3$O | 3-CH$_3$ 4-CH$_3$O | H | C$_2$H$_5$ | 193–194 |
| A22 | 6-CH$_3$O | 3-CH$_3$ 4-i-C$_3$H$_7$O | H | C$_2$H$_5$ | 140–142 |
| A23 | 6-CH$_3$O | 3-CH$_3$ 4-i-C$_4$H$_9$O | H | C$_2$H$_5$ | 144–145 |
| A24 | 7-CH$_3$O | H | CH$_3$ | CH$_3$ | 188–191 |
| A25 | 8-CH$_3$O | H | CH$_3$ | CH$_3$ | 131–133 |
| A26 | 6-C$_2$H$_5$ | H | CH$_3$ | C$_2$H$_5$ | 151–154 |
| A27 | 6-C$_2$H$_5$O | H | H | CH$_3$ | 156–159 |
| A28 | 6-C$_2$H$_5$O | H | CH$_3$ | C$_2$H$_5$ | 165–167 |
| A29 | 6-C$_3$H$_7$ | H | CH$_3$ | CH$_3$ | 127 |
| A30 | 6-C$_3$H$_7$ | H | CH$_3$ | C$_2$H$_5$ | 133–134 |
| A31 | 6-C$_3$H$_7$O | H | CH$_3$ | CH$_3$ | 162–163 |
| A32 | 6-C$_3$H$_7$O | H | CH$_3$ | C$_2$H$_5$ | 136–140 |
| A33 | 5-i-C$_3$H$_7$ | H | CH$_3$ | CH$_3$ | 153–155 |
| A34 | 5-i-C$_3$H$_7$ | H | CH$_3$ | C$_2$H$_5$ | 144 |
| A35 | 6-i-C$_3$H$_7$ | H | H | CH$_3$ | 140–141 |
| A36 | 6-i-C$_3$H$_7$ | H | CH$_3$ | CH$_3$ | 197–199 |
| A37 | 6-i-C$_3$H$_7$ | H | CH$_3$ | C$_2$H$_5$ | 159–165 |
| A38 | 6-i-C$_3$H$_7$ | H | CH$_3$ | i-C$_3$H$_7$ | 184–186 |
| A39 | 6-i-C$_3$H$_7$ | H | CH$_3$O | CH$_3$ | 169–173 |
| A40 | 6-i-C$_3$H$_7$ | H | C$_2$H$_5$ | CH$_3$ | 172 |
| A41 | 6-i-C$_3$H$_7$ | H | C$_2$H$_5$ | C$_2$H$_5$ | 129–130 |
| A42 | 6-i-C$_3$H$_7$ | H | C$_3$H$_7$ | CH$_3$ | 102–103 |
| A43 | 6-i-C$_3$H$_7$ | H | C$_3$H$_7$ | C$_2$H$_5$ | oil |
| A44 | 6-i-C$_3$H$_7$ | H | i-C$_3$H$_7$ | CH$_3$ | 177–179 |
| A45 | 6-i-C$_3$H$_7$ | H | i-C$_3$H$_7$ | C$_2$H$_5$ | 148 |
| A46 | 6-i-C$_3$H$_7$ | H | C$_4$H$_9$ | CH$_3$ | 136–137 |
| A47 | 6-i-C$_3$H$_7$ | H | C$_4$H$_9$ | C$_2$H$_5$ | oil |
| A48 | 6-i-C$_3$H$_7$ | H | C$_6$H$_{13}$ | CH$_3$ | 84–86 |
| A49 | 6-i-C$_3$H$_7$ | H | C$_6$H$_{13}$ | C$_2$H$_5$ | oil |
| A50 | 6-i-C$_3$H$_7$ | H | C$_2$H$_5$OCO | CH$_3$ | 164–165 |
| A51 | 6-i-C$_3$H$_7$ | H | CH$_3$SO$_2$ | CH$_3$ | 245–247 |
| A52 | 6-i-C$_3$H$_7$ | H | CN | CH$_3$ | 250–251 |
| A53 | 6-i-C$_3$H$_7$ | H | CH$_3$CO | CH$_3$ | 169–171 |
| A54 | 6-i-C$_3$H$_7$ | 3-Cl | CH$_3$ | C$_2$H$_5$ | 159–160 |
| A55 | 6-i-C$_3$H$_7$ | 4-Cl | H | CH$_3$ | 149–152 |

TABLE I-continued

| Compound No. | R₁ | X | R₃' | R₄ | m.p.(° C.) |
|---|---|---|---|---|---|
| A56 | 6-i-C₃H₇ | 4-Cl | H | C₂H₅ | 172–173 |
| A57 | 6-i-C₃H₇ | 4-Cl | CH₃ | CH₃ | 231–232 |
| A58 | 6-i-C₃H₇ | 4-Cl | CH₃ | C₂H₅ | 204–205 |
| A59 | 6-i-C₃H₇ | 3-F | CH₃ | CH₃ | 263 |
| A60 | 6-i-C₃H₇ | 3-F | CH₃ | C₂H₅ | 174–175 |
| A61 | 6-i-C₃H₇ | 3,4-diCl | H | CH₃ | 207–210 |
| A62 | 6-i-C₃H₇ | 3,4-diCl | CH₃ | CH₃ | 268–270 |
| A63 | 6-i-C₃H₇ | 3,4-diCl | H | C₂H₅ | 160–162 |
| A64 | 6-i-C₃H₇ | 3,4-diCl | CH₃ | C₂H₅ | 197–198 |
| A65 | 6-i-C₃H₇ | 3,4-diF | CH₃ | CH₃ | 278–279 |
| A66 | 6-i-C₃H₇ | 3,4-diF | CH₃ | C₂H₅ | 194–196 |
| A67 | 6-i-C₃H₇ | 3-CF₃ | CH₃ | CH₃ | 200–201 |
| A68 | 6-i-C₃H₇ | 3-CF₃ | CH₃ | C₂H₅ | 179 |
| A69 | 6-i-C₃H₇ | 4-CF₃ | CH₃ | CH₃ | >300 |
| A70 | 6-i-C₃H₇ | 4-CF₃ | CH₃ | C₂H₅ | 218–219 |
| A71 | 6-i-C₃H₇ | 2-OH | H | CH₃ | >300 |
| A72 | 6-i-C₃H₇ | 3-OH | H | CH₃ | 248–249 |
| A73 | 6-i-C₃H₇ | 4-OH | H | CH₃ | >300 |
| A74 | 6-i-C₃H₇ | 4-OH | CH₃ | CH₃ | >300 |
| A75 | 6-i-C₃H₇ | 2-CH₃ | CH₃ | C₂H₅ | 157–159 |
| A76 | 6-i-C₃H₇ | 3-CH₃ | CH₃ | CH₃ | 181–183 |
| A77 | 6-i-C₃H₇ | 3-CH₃ | CH₃ | C₂H₅ | 140–144 |
| A78 | 6-i-C₃H₇ | 3-CH₃O | CH₃ | C₂H₅ | 130–132 |
| A79 | 6-i-C₃H₇ | 4-CH₃ | CH₃ | CH₃ | 180–181 |
| A80 | 6-i-C₃H₇ | 4-CH₃ | CH₃ | C₂H₅ | 171–172 |
| A81 | 6-i-C₃H₇ | 4-CH₃O | CH₃ | CH₃ | 177–178 |
| A82 | 6-i-C₃H₇ | 4-CH₃O | CH₃ | C₂H₅ | 193–196 |
| A83 | 6-i-C₃H₇ | 4-CH₃O | CH₃ | C₃H₇ | 199–202 |
| A84 | 6-i-C₃H₇ | 4-C₂H₅ | CH₃ | CH₃ | 193–194 |
| A85 | 6-i-C₃H₇ | 4-C₂H₅ | CH₃ | C₂H₅ | 148–150 |
| A86 | 6-i-C₃H₇ | 4-C₂H₅O | CH₃ | CH₃ | 169–170 |
| A87 | 6-i-C₃H₇ | 4-C₂H₅O | CH₃ | C₂H₅ | 173–175 |
| A88 | 6-i-C₃H₇ | 4-C₃H₇ | CH₃ | CH₃ | 181–183 |
| A89 | 6-i-C₃H₇ | 4-C₃H₇ | CH₃ | C₂H₅ | 88–91 |
| A90 | 6-i-C₃H₇ | 4-C₃H₇O | CH₃ | CH₃ | 164–166 |
| A91 | 6-i-C₃H₇ | 4-C₃H₇O | CH₃ | C₂H₅ | 125–127 |
| A92 | 6-i-C₃H₇ | 4-C₅H₁₁ | CH₃ | CH₃ | 159–160 |
| A93 | 6-i-C₃H₇ | 4-C₅H₁₁ | CH₃ | C₂H₅ | 110–113 |
| A94 | 6-i-C₃H₇ | 4-C₅H₁₁O | CH₃ | CH₃ | 137–138 |
| A95 | 6-i-C₃H₇ | 4-C₅H₁₁O | CH₃ | C₂H₅ | 255–257 |
| A96 | 6-i-C₃H₇ | 3-CH₃ 4-OH | H | CH₃ | 248–250 |
| A97 | 6-i-C₃H₇ | 3-CH₃ 4-CH₃O | H | CH₃ | 209–210 |
| A98 | 6-i-C₃H₇ | 3-CH₃ 4-CH₃O | H | CH₃ | 128–129 |
| A99 | 6-i-C₃H₇ | 3-CH₃ 4-C₂H₅O | H | CH₃ | 134–135 |
| A100 | 6-i-C₃H₇ | 3-CH₃ 4-i-C₃H₇O | H | CH₃ | 130–131 |
| A101 | 6-i-C₃H₇ | 3-CH₃O 4-OH | H | CH₃ | 293–295 |
| A102 | 6-i-C₃H₇ | 3-C₂H₅ 4-CH₃O | H | CH₃ | 155–157 |
| A103 | 6-i-C₃H₇ | 3-C₂H₅ 4-i-C₃H₇O | H | CH₃ | 147–150 |
| A104 | 6-i-C₃H₇ | 3-C₂H₅ 4-CH₃COO | H | CH₃ | 149–153 |
| A105 | 6-i-C₃H₇ | 3-i-C₃H₇ 4-CH₃O | H | CH₃ | 180–182 |
| A106 | 6-i-C₃H₇ | 2,3-diCH₃ | CH₃ | CH₃ | 185–187 |
| A107 | 6-i-C₃H₇ | 2,4-diCH₃ | CH₃ | CH₃ | 151–152 |
| A108 | 6-i-C₃H₇ | 2,4-diCH₃ | CH₃ | C₂H₅ | 121 |
| A109 | 6-i-C₃H₇ | 2,5-diCH₃ | CH₃ | CH₃ | 143–145 |
| A110 | 6-i-C₃H₇ | 3,4-diCH₃ | CH₃ | CH₃ | 154–156 |
| A111 | 6-i-C₃H₇ | 3,4-diCH₃ | CH₃ | C₂H₅ | 119–121 |
| A112 | 6-i-C₃H₇ | 3,5-diCH₃ | CH₃ | C₂H₅ | 151–155 |
| A113 | 6-i-C₃H₇ | 3-OH 4-CH₃ | CH₃ | CH₃ | 295 |
| A114 | 6-i-C₃H₇ | 3-OH 4-CH₃O | CH₃ | CH₃ | 227–228 |
| A115 | 6-i-C₃H₇ | 3-CH₃ 4-CH₃O | CH₃ | C₂H₅ | 158–160 |
| A116 | 6-i-C₃H₇ | 3-CH₃ 4-CH₃O | C₂H₅OCO | C₂H₅ | 179–180 |
| A117 | 6-i-C₃H₇ | 3-CH₃O 4-CH₃ | CH₃ | CH₃ | 166 |
| A118 | 6-i-C₃H₇ | 3-CH₃O 4-CH₃ | CH₃ | C₂H₅ | 164–166 |
| A119 | 6-i-C₃H₇O | 3-CH₃ 4-CH₃O | H | C₂H₅ | 177–178 |
| A120 | 6-i-C₃H₇O | 3-CH₃ 4-i-C₃H₇O | H | C₂H₅ | 123–124 |
| A121 | 7-i-C₃H₇ | H | CH₃ | CH₃ | 156–157 |
| A122 | 7-i-C₃H₇ | H | CH₃ | C₂H₅ | 142–144 |
| A123 | 7-i-C₄H₇O | H | CH₃ | CH₃ | 179–182 |
| A124 | 6-C₄H₉ | H | CH₃ | CH₃ | 140 |
| A125 | 6-C₄H₉ | H | CH₃ | C₂H₅ | 85–86 |
| A126 | 6-C₄H₉O | H | CH₃ | CH₃ | 126–128 |
| A127 | 6-C₄H₉O | H | CH₃ | C₂H₅ | 136–138 |
| A128 | 6-i-C₄H₉ | H | CH₃ | CH₃ | 121–125 |
| A129 | 6-i-C₄H₉O | H | CH₃ | CH₃ | oil |
| A130 | 6-i-C₄H₉O | H | CH₃ | C₂H₅ | 106–107 |
| A131 | 6-i-C₄H₉O | H | CH₃ | 2-butenyl | 97–101 |
| A132 | 6-i-C₄H₉O | H | CH₃ | benzyl | 178–181 |
| A133 | 6-i-C₄H₉O | 3-CH₃ 4-CH₃O | H | CH₃ | 167–168 |
| A134 | 6-i-C₄H₉O | 3-CH₃ 4-CH₃O | H | C₂H₅ | 169–170 |
| A135 | 6-i-C₄H₉O | 3-CH₃ 4-CH₃O | CH₃ | C₂H₅ | 180–182 |
| A136 | 6-i-C₄H₉O | 3-CH₃ 4-C₄H₉O | H | C₂H₅ | 116–118 |
| A137 | 6-C₅H₁₁ | H | CH₃ | CH₃ | 138–140 |
| A138 | 6-C₅H₁₁ | H | CH₃ | C₂H₅ | 94–96 |
| A139 | 6-C₅H₁₁O | H | CH₃ | CH₃ | 115–117 |
| A140 | 6-i-C₅H₁₁ | H | CH₃ | CH₃ | 138–139 |
| A141 | 6-i-C₅H₁₁ | H | CH₃ | C₂H₅ | 101–103 |
| A142 | 6-i-C₅H₁₁O | H | CH₃ | CH₃ | 112–113 |
| A143 | 6-i-C₅H₁₁O | H | CH₃ | C₂H₅ | 128–130 |
| A144 | 6-C₅H₁₃ | H | CH₃ | CH₃ | 123–125 |
| A145 | 6-C₅H₁₃ | H | CH₃ | C₂H₅ | oil |
| A146 | 6-C₅H₁₃O | H | CH₃ | CH₃ | 100–102 |
| A147 | 6-C₅H₁₃O | H | CH₃ | C₂H₅ | 96–98 |
| A148 | 6-i-C₅H₁₃O | H | CH₃ | CH₃ | 106–109 |
| A149 | 6-C₈H₁₇ | H | CH₃ | CH₃ | 105–107 |
| A150 | 6-C₈H₁₇ | H | CH₃ | C₂H₅ | oil |
| A151 | 6-cyclohexyl | H | CH₃ | CH₃ | 221–222 |
| A152 | 6-cyclohexyl | H | CH₃ | C₂H₅ | 154–156 |
| A153 | 6-NO₂ | H | CH₃ | CH₃ | 279(dec) |
| A154 | 6-NH₂ | H | CH₃ | CH₃ | 227 |
| A155 | 6-(CH₃)₂N | H | CH₃ | CH₃ | 179–183 |
| A156 | 6-N-(2-dimethyl aminoethyl-amino) | H | CH₃ | C₃ | methyl-iodide 285(dec) |
| A157 | 6-i-C₄H₉NH | H | CH₃ | CH₃ | 183–186 |
| A158 | Compound No.157 2HCl/·1/2H₂O | | | | 194(dec) |
| A159 | 6-i-C₄H₉NH | H | CH₃ | C₂H₅ | H₂O 162 |
| A160 | 6-i-C₄H₉NH | H | CH₃ | CH₃ | HCl 183 |
| A161 | 6-pyrrolidino | H | CH₃ | CH₃ | 157–167 |
| A162 | 6-pyrrolidino | H | CH₃ | C₂H₅ | 122–130 |
| A163 | 6-piperazino | H | CH₃ | CH₃ | 186–196 |
| A164 | 6-piperazino | H | CH₃ | C₂H₅ | 186–189 |
| A165 | 6-(4-methyl piperazino) | H | CH₃ | C₂H₅ | 111–113 |
| A166 | 6-(4-acetyl piperazino) | H | CH₃ | CH₃ | 220–225 |
| A167 | 6-(4-acetyl piperazino) | H | CH₃ | C₂H₅ | 200–204 |
| A168 | 6-morpholino | H | CH₃ | CH₃ | 241–243 |
| A169 | 6-morpholino | H | CH₃ | C₂H₅ | 195–196 |
| A170 | 6-C₆H₅ | H | CH₃ | CH₃ | 164–169 |
| A171 | 6-C₆H₅ | H | CH₃ | C₂H₅ | 192–194 |
| A172 | 6-(3-pyridyl) | H | H | CH₃ | oil |
| A173 | 6-Cl | H | CH₃ | CH₃ | 187–189 |
| A174 | 6-Cl | H | CH₃ | C₂H₅ | 160–161 |
| A175 | 6-F | H | CH₃ | CH₃ | 192–193 |

TABLE I-continued

| Compound No. | R₁ | X | R₃' | R₄ | m.p.(° C.) |
|---|---|---|---|---|---|
| A176 | 6-F | H | CH₃ | C₂H₅ | 193–196 |
| A177 | 7-F | H | CH₃ | CH₃ | 219–221 |
| A178 | 5-Cl 6-i-C₄H₉O | H | CH₃ | CH₃ | 207–208 |
| A179 | 5-Cl 6-i-C₄H₉O | H | CH₃ | C₂H₅ | 174–176 |
| A180 | 5-Cl 6-i-C₄H₉O | 3-CH₃ | CH₃ | CH₃ | 179–180 |
| A181 | 5-Cl 6-i-C₄H₉O | 3-CH₃ | CH₃ | C₂H₅ | 167–167 |
| A182 | 5-F 6-i-C₄H₉O | H | CH₃ | CH₃ | 172–173 |
| A183 | 5-F 6-i-C₄H₉O | 4-C₂H₅ | CH₃ | CH₃ | 205–207 |
| A184 | 5-CH₃ 6-CH₃O | 3-CH₃ 4-CH₃O | CH₃ | C₂H₅ | 165–167 |
| A185 | 5-CH₃ 6-i-C₃H₇O | 3-CH₃ 4-i-C₃H₇O | CH₃ | C₂H₅ | 175–176 |
| A186 | 5-CH₃ 6-i-C₄H₉O | H | H | CH₃ | 127 |
| A187 | 5-CH₃ 6-i-C₄H₉O | H | H | C₂H₅ | 182–184 |
| A188 | 5-CH₃ 6-i-C₄H₉O | H | CH₃ | C₂H₅ | 154–156 |
| A189 | 5-CH₃ 6-i-C₄H₉O | 3-CH₃ 4-CH₃O | H | C₂H₅ | 185–186 |
| A190 | 5-CH₃ 6-i-C₄H₉O | 3-CH₃ 4-CH₃O | CH₃ | CH₃ | 150–151 |
| A191 | 5-CH₃ 6-i-C₄H₉O | 3-CH₃ 4-CH₃O | CH₃ | C₂H₅ | 149 |
| A192 | 5-CH₃ 6-i-C₄H₉O | 3-CH₃ 4-i-C₃H₇O | CH₃ | C₂H₅ | 169–171 |
| A193 | 5-CH₃ 6-i-C₄H₉O | 3-CH₃ 4-i-C₃H₇O | H | C₂H₅ | 114–115 |
| A194 | 5-NH₂ 6-i-C₄H₉O | H | CH₃ | CH₃ | HCl 130–131 |
| A195 | 5-i-C₃H₇ 6-CH₃O | H | CH₃ | CH₃ | 153–155 |
| A196 | 5-CH₃O 6-i-C₄H₉O | H | CH₃ | CH₃ | 130–131 |
| A197 | 5-i-C₄H₉O 6-F | H | CH₃ | CH₃ | oil |
| A198 | 5-[N-methyl-N-(2-dimethyl-amino-ethyl)amino] 6-F | H | CH₃ | CH₃ | 120–122 |
| A199 | 5,7-diF | H | CH₃ | CH₃ | 218–220 |
| A200 | 5,7-diCH₃O | H | CH₃ | CH₃ | 220 |
| A201 | 5-i-C₄H₉O 7-F | H | CH₃ | CH₃ | 120 |
| A202 | 6,7-diF | H | CH₃ | CH₃ | 194–197 |
| A203 | 6-F 7-i-C₄H₉O | H | CH₃ | CH₃ | 216–219 |
| A204 | 6-F 7-piperidino | H | CH₃ | CH₃ | 189–194 |
| A205 | 6-F,7-(4-hydroxy-piperidino) | H | CH₃ | CH₃ | >300 |
| A206 | 6-F 7-pyrrolidino | H | CH₃ | CH₃ | 221–225 |
| A207 | 6-F 7-morpholino | H | CH₃ | CH₃ | 251–252 |
| A208 | 6-F 7-piperazino | H | CH₃ | CH₃ | 223–226 |
| A209 | 6-F 7-(4-methyl-piperazino) | H | CH₃ | CH₃ | 202–205 |
| A210 | 6-F 7-(4-acetyl-piperadino) | H | CH₃ | CH₃ | 215–218 |
| A211 | 6-F, 7-[N-methyl-N-(2-hydroxy-ethyl)amino | H | CH₃ | CH₃ | 189–190 |
| A212 | 6-OH 7-F | H | CH₃ | CH₃ | >300 |
| A213 | 6-OH 7-i-C₃H₇ | H | CH₃ | CH₃ | >300 |
| A214 | 6-CH₃O 7-F | H | CH₃ | CH₃ | 210–213 |
| A215 | 6-C₂H₅O 7-F | H | CH₃ | CH₃ | 266–267 |
| A216 | 6-C₃H₇O 7-F | H | CH₃ | CH₃ | 198–200 |
| A217 | 6-C₄H₉O 7-F | H | CH₃ | CH₃ | 146–148 |
| A218 | 6,7-OCH₂O— | H | CH₃ | CH₃ | 185–189 |
| A219 | 6,7-OC₂H₄N-(CH₃)— | H | CH₃ | CH₃ | 273–274 |
| A220 | 6,7-diCH₃O | H | CH₃ | CH₃ | 282–283 |
| A221 | 6,7-diC₂H₅O | H | CH₃ | CH₃ | 219–221 |
| A222 | 6,7-diC₃H₇O | H | CH₃ | CH₃ | 187–189 |
| A223 | 6,7-di-i-C₄H₉O | H | CH₃ | CH₃ | 218–220 |
| A224 | 6-CH₃O 7-C₂H₅ | H | CH₃ | CH₃ | 202–206 |
| A225 | 6-CH₃O 7-C₃H₇ | H | CH₃ | CH₃ | 175–177 |
| A226 | 6-CH₃O 7-i-C₃H₇ | H | CH₃ | CH₃ | 174–177 |
| A227 | 6-CH₃O 7-i-C₃H₇ | H | CH₃ | C₂H₅ | 133–134 |
| A228 | 6-CH₃O 7-i-C₃H₇ | 4-C₂H₅ | CH₃ | CH₃ | 172–175 |
| A229 | 6-CH₃O 7-i-C₃H₇ | 4-i-C₃H₇ | CH₃ | CH₃ | 182–183 |
| A230 | 6-CH₃O 7-i-C₃H₇ | 3-CH₃ 4-CH₃O | H | CH₃ | 197–199 |
| A231 | 6-CH₃O 7-i-C₃H₇ | 3-CH₃ 4-CH₃O | CH₃ | CH₃ | 200 |
| A232 | 6-CH₃O 7-i-C₃H₇ | 3-CH₃ 4-CH₃O | CH₃ | C₂H₅ | 170–171 |
| A233 | 6-i-C₄H₉O 7-CH₃ | H | H | CH₃ | 156–157 |
| A234 | 6-i-C₄H₉O 7-CH₃ | H | CH₃ | CH₃ | 202–204 |
| A235 | 6-i-C₄H₉O 7-CH₃ | H | CH₃ | C₂H₅ | 142–144 |
| A236 | 6-i-C₄H₉O 7-CH₃ | 3-CH₃ 4-CH₃O | H | CH₃ | 219–220 |
| A237 | 6-i-C₄H₉O 7-CH₃ | 3-CH₃ 4-CH₃O | CH₃ | CH₃ | 178–179 |
| A238 | 6-i-C₄H₉O 7-CH₃ | 3-CH₃ 4-CH₃O | CH₃ | C₂H₅ | 196 |
| A239 | 6-CH₃O 7-C₂H₅O | H | CH₃ | CH₃ | 239–242 |
| A240 | 6-CH₃O 7-C₃H₇O | H | CH₃ | CH₃ | 215–222 |
| A241 | 6-CH₃O 7-i-C₄H₉O | H | CH₃ | CH₃ | 213–216 |
| A242 | 6-CH₃O 7-CF₃ | H | CH₃ | CH₃ | 210–213 |
| A243 | 6-CH₃O 7-cyclohexyloxy | H | CH₃ | CH₃ | 229–231 |

TABLE I-continued

| Compound No. | $R_1$ | X | $R_3'$ | $R_4$ | m.p.(° C.) |
|---|---|---|---|---|---|
| A244 | 6-CH$_3$O 7-C$_6$H$_5$O | H | CH$_3$ | CH$_3$ | 216–218 |
| A245 | 6-CH$_3$O 7-(4-pyridyl)oxy | H | CH$_3$ | CH$_3$ | >300 |
| A246 | 6-CH$_3$O 7-pyrrolidino | H | CH$_3$ | CH$_3$ | 215–217 |
| A247 | 6-CH$_3$O 7-piperidino | H | CH$_3$ | CH$_3$ | 230–237 |
| A248 | 6-CH$_3$O 7-morpholino | H | CH$_3$ | CH$_3$ | 246–248 |
| A249 | 6-CH$_3$O 7-thiomorpholino | H | CH$_3$ | CH$_3$ | 234–236 |
| A250 | 6-CH$_3$O 7-piperazino | H | CH$_3$ | CH$_3$ | 217–220 |
| A251 | 6-CH$_3$O 7-(4-methylpiperazino) | H | CH$_3$ | CH$_3$ | 231–233 |
| A252 | 6-CH$_3$O 7-(4-acetylpiperazino) | H | CH$_3$ | CH$_3$ | 247–249 |
| A253 | 6-CH$_3$O 7-pyrrolyl | H | CH$_3$ | CH$_3$ | 252–254 |
| A254 | 6-CH$_3$O 7-(1-pyrazolyl) | H | CH$_3$ | CH$_3$ | 180–182 |
| A255 | 6-CH$_3$O 7-(1-imidazolyl) | H | CH$_3$ | CH$_3$ | 254–257 |
| A256 | 6-CH$_3$O 7-(1-triazolyl) | H | CH$_3$ | CH$_3$ | 241–245 |
| A257 | 6-C$_2$H$_5$O 7-i-C$_3$H$_7$ | H | CH$_3$ | CH$_3$ | 128–130 |
| A258 | 6-i-C$_3$H$_7$O 7-i-C$_3$H$_7$ | H | CH$_3$ | CH$_3$ | 126–128 |
| A259 | 6-i-C$_3$H$_7$O 7-i-C$_3$H$_7$ | H | CH$_3$ | CH$_3$ | 126–128 |
| A260 | 6-i-C$_4$H$_9$O 7-CH$_3$O | H | CH$_3$ | CH$_3$ | 241–242 |
| A261 | 6-i-C$_4$H$_9$O 7-i-C$_3$H$_7$ | H | CH$_3$ | CH$_3$ | 134–137 |
| A262 | 6-i-C$_4$H$_9$O 7-CF$_3$ | H | CH$_3$ | CH$_3$ | 176–177 |
| A263 | 6-i-C$_4$H$_9$O 7-pyrrolidino | H | CH$_3$ | CH$_3$ | 198–203 |
| A264 | 6-i-C$_4$H$_9$O 7-piperidino | H | CH$_3$ | CH$_3$ | 224–225 |
| A265 | 6-i-C$_4$H$_9$O 7-morpholino | H | CH$_3$ | CH$_3$ | 216–219 |
| A266 | 6-acetoxy 7-CH$_3$ | H | CH$_3$ | CH$_3$ | 139 |
| A267 | 6-hydroxycarbonyloxy 7-CH$_3$ | H | CH$_3$ | CH$_3$ | >300 |
| A268 | 6-ethoxycarbonyloxy 7-CH$_3$ | H | CH$_3$ | CH$_3$ | 169–170 |
| A269 | 6-hydroxycarbonylmethoxy 7-CH$_3$ | H | CH$_3$ | CH$_3$ | >300 |
| A270 | 6-i-C$_3$H$_7$ 7-CH$_3$O | H | CH$_3$ | C$_2$H$_5$ | 232 |
| A271 | 6-ethoxycarbonyloxy 7-i-C$_3$H$_7$ | H | CH$_3$ | CH$_3$ | 183–184 |
| A272 | 7,8-diF | H | CH$_3$ | CH$_3$ | 226–228 |
| A273 | 7-i-C$_3$H$_7$ 8-CH$_3$O | H | CH$_3$ | CH$_3$ | 144–145 |
| A274 | 7-i-C$_3$H$_7$ 8-CH$_3$O | 4-C$_2$H$_5$ | CH$_3$ | CH$_3$ | 152–155 |
| A275 | 7-i-C$_4$H$_9$ 8-F | H | CH$_3$ | CH$_3$ | oil |
| A276 | 5,7-diCl 8-CH$_3$O | H | CH$_3$ | CH$_3$ | 223–226 |
| A277 | 5,7-diCl 6-CH$_3$O | H | CH$_3$ | C$_2$H$_5$ | 180–182 |
| A278 | 5,7-diCl 6-i-C$_4$H$_9$O | H | CH$_3$ | CH$_3$ | 196–199 |
| A279 | 5,7-diCl 6-i-C$_4$H$_9$O | H | CH$_3$ | C$_2$H$_5$ | 193–194 |
| A280 | 5-Cl 6-CH$_3$O 7-i-C$_3$H$_7$ | H | CH$_3$ | CH$_3$ | 184–186 |
| A281 | 5-Cl 6-CH$_3$O 7-i-C$_3$H$_7$ | H | CH$_3$ | C$_2$H$_5$ | 154–155 |
| A282 | 5-Cl 6-i-C$_4$H$_9$O 7-CH$_3$ | H | CH$_3$ | CH$_3$ | 188–189 |
| A283 | 5-Cl 6-i-C$_4$H$_9$O 7-CH$_3$ | H | CH$_3$ | C$_2$H$_5$ | 205–207 |
| A284 | 5-Cl 6-i-C$_4$H$_9$O 7-Cl | H | CH$_3$ | CH$_3$ | 183–186 |
| A285 | 5,7-diCH$_3$ 6-i-C$_4$H$_9$O | H | H | CH$_3$ | 170–172 |
| A286 | 5,7-diCH$_3$ 6-i-C$_4$H$_9$O | H | CH$_3$ | CH$_3$ | 158–160 |
| A287 | 5,7-diCH$_3$ 6-i-C$_4$H$_9$O | H | CH$_3$ | C$_2$H$_5$ | 175–178 |
| A288 | 5,7-diCH$_3$ 6-i-C$_4$H$_9$O | 3-CH$_3$ 4-CH$_3$O | CH$_3$ | CH$_3$ | 155–157 |
| A289 | 5,7-diCH$_3$ 6-i-C$_4$H$_9$O | 3-CH$_3$ 4-CH$_3$O | CH$_3$ | C$_2$H$_5$ | 154–157 |

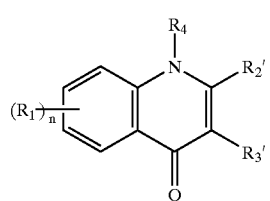

$R_2'$ = non-phenyl

TABLE II

| Compound No. | $R_1$ | $R_2'$ | $R_3'$ | $R_4$ | m.p. (° C.) |
|---|---|---|---|---|---|
| A290 | 6-$C_3H_7$ | $CH_3$ | $C_6H_5$ | $CH_3$ | 241–245 |
| A291 | 6-i-$C_3H_7$ | $CH_3$ | $CH_3$ | $CH_3$ | 188–189 |
| A292 | 6-i-$C_3H_7$ | $CH_3$ | $C_4H_9$ | $CH_3$ | 106–107 |
| A293 | 6-i-$C_3H_7$ | $CH_3$ | $C_4H_9$ | $C_2H_5$ | oil |
| A294 | 6-i-$C_3H_7$ | $C_3H_7$ | H | $CH_3$ | 132–134 |
| A295 | 6-i-$C_3H_7$ | 2-pyridyl | H | $CH_3$ | 124–126 |
| A296 | 6-i-$C_3H_7$ | 2-pyridyl | H | $C_2H_5$ | 144–146 |
| A297 | 6-i-$C_3H_7$ | 3-pyridyl | H | $CH_3$ | 164–166 |
| A298 | 6-i-$C_3H_7$ | 3-pyridyl | H | $C_2H_5$ | 148–149 |
| A299 | 6-i-$C_3H_7$ | 3-pyridyl | $CH_3$ | $CH_3$ | 242–243 |
| A300 | 6-i-$C_3H_7$ | 4-pyridyl | H | $CH_3$ | 192–193 |
| A301 | 6-i-$C_3H_7$ | 4-pyridyl | H | $C_2H_5$ | 229–230 |
| A302 | 6-i-$C_3H_7$ | 2-pyradinyl | H | $C_2H_5$ | 94–96 |
| A303 | 6-i-$C_3H_7$ | 2-furyl | H | $CH_3$ | 86–88 |
| A304 | 6-i-$C_3H_7$ | 2-furyl | H | $C_2H_5$ | 70–73 |
| A305 | 6-i-$C_3H_7$ | N—$CH_3$-2-pyrrolyl | H | $C_2H_5$ | 101–104 |
| A306 | 6-i-$C_3H_7$ | N—$CH_3$-3-pyrrolyl | H | $CH_3$ | 173–176 |
| A307 | 6-i-$C_3H_7$ | N—$CH_3$-3-pyrrolyl | H | $C_2H_5$ | 132–134 |
| A308 | 6-i-$C_3H_7$ | 2-thienyl | H | $CH_3$ | 111–113 |
| A309 | 6-i-$C_3H_7$ | 2-thienyl | H | $C_2H_5$ | 95–96 |
| A310 | 6-i-$C_3H_7$ | 2-thienyl | $CH_3$ | $CH_3$ | 136–137 |
| A311 | 6-i-$C_3H_7$ | 2-thienyl | $CH_3$ | $C_2H_5$ | 169–173 |
| A312 | 6-i-$C_3H_7$ | 3-thienyl | H | $CH_3$ | 164–166 |
| A313 | 6-i-$C_3H_7$ | 3-thienyl | H | $C_2H_5$ | 118–120 |
| A314 | 6-i-$C_3H_7$ | 5-$CH_3$-2-thienyl | H | $CH_3$ | 132 |
| A315 | 6-i-$C_3H_7$ | 5-$CH_3$-2-thienyl | H | $C_2H_5$ | 121–122 |
| A316 | 6-i-$C_3H_7$ | 5-Br-2-thienyl | H | $CH_3$ | 183–185 |
| A317 | 6-i-$C_3H_7$ | 5-Br-2-thienyl | H | $C_2H_5$ | oil |
| A318 | 5-$CH_3$ 6-i-$C_4H_9O$ | 2-thiernyl | $CH_3$ | $CH_3$ | 111–112 |
| A319 | 6-i-$C_3H_7$ | 2-thiazolyl | H | $C_2H_5$ | 91–93 |
| A320 | 6-i-$C_3H_7$ | $C_6H_5$ | $CH_3$ | $C_6H_5$ | 225 |
| A321 | 6-i-$C_3H_7$ | $C_6H_5$ | $CH_3$ | 2-F—$C_6H_4$ | 205–207 |
| A322 | 6-i-$C_3H_7$ | $C_6H_5$ | $CH_3$ | 3-F—$C_6H_4$ | 248–251 |
| A323 | 6-i-$C_3H_7$ | $C_6H_5$ | $CH_3$ | 4-F—$C_6H_4$ | 224–229 |
| A324 | 6-i-$C_3H_7$ | $C_6H_5$ | $CH_3$ | 4-Cl—$C_6H_4$ | 233–235 |
| A325 | 6-i-$C_3H_7$ | $C_6H_5$ | $CH_3$ | 4-$CH_3$—$C_6H_4$ | 203–205 |
| A326 | 6-i-$C_3H_7$ | $C_6H_5$ | $CH_3$ | 4-$CH_3O$—$C_6H_4$ | 204–208 |

Part B.

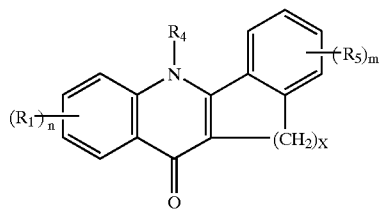

(XVIII)

Example 7

5-Ethyl-8-isopropyl-5,10-dihydro-11H-indeno[1,2-b]quinolin-10-one(Compound B2)

To a 1.6M solution of n-butyl lithium in hexane (6.6 mL, 10.5 mmol) was added tetramethylethylenediamine (1.58 mL, 10.5 mmol) under argon atomosphere at room temperature with stirring. To this was added with ice cooling a solution of 1-indanone (1.38 g, 10.5 mmol) in anhydrous THF followed by stirring at room temperature for 1 hour. After ice cooling the mixture, a solution of 1-ethyl-6-isopropylisatoic anhydride prepared in step 1 of Example 6 (1.22 g, 5.2 mmol) in anhydrous THF was added dropwise thereto. The mixture was stirred at room temperature overnight and then duluted with saturated aqueous solution of ammonium chloride. The organic layer was separated and concentrated in vacuo. The residue was dissolved in ethyl acetate, washed with saturated sodium chloride solution and dried with sodium sulfate followed by evaporating to remove the solvent. The residue was purified by silica gel-chromatography (chloroform) and crystallization from diethyl ether to obtain the desired compound. $^1$H-NMR (CDCl$_3$) δ 1.32(6H,d,CH(CH$_3$)$_2$), 1.70(3H,t,CH$_2$CH$_3$), 3.09 (1H,septet,CH), 3.91(2H,s,H-11), 4.71(2H,q,NCH$_2$), 7.47–7.94(6H,m,Ar-H), 8.44(1H,s,H-9)

Example 8

2.5-Diethyl-8-isopropyl-5,10-dihydro-11H-indeno[1,2-b]quinolin-10-one (Compound B9)

Step 1. 3-Chloro-1-(4-ethylphenyl)-1-propanone

To a solution of anhydrous aluminum chloride (20 g, 0.15 mmol) in nitrobenzene(50 mL) was added dropwise a solution (30 mL) of ethylbenzene(13.5 mL, 0.11 mmol) and 3-chloropropionyl chloride (25 g, 0.20 mmol) in nitrobenzene. The mixture was stirred at room temperature for 3 hours and then poured into ice-water (600 mL) containing 100 mL of concentrated hydrochloric acid followed by extraction with diethyl ether. The combined organic layers were washed with water and saturated sodium chloride solution, dried with sodium sulfate and evoparated to remove diethyl ether and nitrobenzene under reduced pressure. The residue was crystallized from n-hexane to give the title compound (9.1 g, 42.1%). $^1$H-NMR(CDCl$_3$) δ 1.26(3H, t,CH$_2$CH$_3$), 2.72(2H,q,CH$_2$CH$_3$), 3.44(2H,t,COCH$_2$), 3.93 (2H,t,CH$_2$Cl), 7.31(2H,d,Ar-H), 7.89(2H,d,Ar-H)

Step 2. 5-Ethyl-1-indanone

3-Chloro-1-(4-ethylphenyl)-1-propanone (9.1 g, 46.3 mmol) was dissolved in 50 mL of conc. H$_2$SO$_4$ and heated at 100° C. for 30 minutes with stirring. The reaction mixture was poured onto crashed ice (500 g). The resulting precipitate was filtered off, washed with water and then dissolved in diethyl ether. The solution was washed with water and saturated sodium chloride solution, dried with sodium sulfate and evaporated to dryness. The title compound was obtained by crystallizing the residue from n-hexane. $^1$H-NMR(CDCl$_3$)δ 1.28(3H,t,CH$_2$CH$_3$), 2.67–2.70(2H,m, H-3), 2.74(2H,q,CH$_2$CH$_3$), 3.11(2H,dd,H-2), 7.21(1H,d,Ar-H), 7.30(1H,s,H-4), 7.68(1H,d,Ar-H)

Step 3. 2,5-Diethyl-8-isopropyl-5,10-dihydro-11H-indeno[1,2-b]quinolin-10-one

To a 1.53M solution of n-butyl lithium in hexane (13.2 mL, 20.2 mmol) was added TMEDA (3.1 mL, 20.2 mmol) under argon atmosphere at room temperature with stirring. To this was added with ice cooling a solution of 5-ethyl-1-indanone(3.24 g, 20.2 mmol) in anhydrous THF followed by stirring at room temperature for 1 hour. After ice cooling the mixture, a solution of 1-ethyl-6-isopropylisatoic anhydride (Example 6, step 1) (2.35 g, 10.1 mmol) in anhydrous THF was added dropwise thereto. The mixture was stirred at room temperature overnight and diluted with saturated aqueous solution of ammonium chloride. The orgaic layer was separated and concentrated in vacuo. The residue was dissolved in ethyl acetate, washed with saturated sodium chloride solution and dried with sodium sulfate. After removing the solvent, the residue was purified by silica gel-chromatography (chloroform:acetone=20:1) and crystallization from diethyl ether to give the desired compound. $^1$H-NMR(CDCl$_3$) δ 1.32(3H,t,CH$_2$CH$_3$), 1.34(6H,d,CH(CH$_3$)$_2$), 1.70(3H,t,NCH$_2$CH$_3$), 2.78(2H,q,CH$_2$CH$_3$), 3.10 (1H,septet,CH), 3.91(2H,s,H-11), 4.72(2H,q,NCH$_2$), 7.30–7.85(5H,m,Ar-H), 8.45(1H,s,H-9)

Example 9.

2-Ethyl-9-isopropyl-6,12-dihydrobenzo[c]acridin-7(5H)-one (Compund B25)

To a 1.6M solution of n-butyl lithium in hexane (1.6 mL, 2.6 mmol) was added TMEDA (0.4 mL, 2.6 mmol) under argon atmosphere at room temperature with stirring. To this was added with ice cooling a solution of 1-tetralone (0.38 g, 2.6 mmol) in anhydrous THF followed by stirring for 1 hour under ice cooling. Thereafter, a solution of 1-ethyl-6-1-propylisatoic anhydride (0.3 g, 1.3 mmol) in anhydrous THF was added dropwise followed by stirring at room temperature for 1.5 hours. The reaction mixture was diluted with saturated aqueous solution of ammonium chloride. The organic layer was separated and concentrated under reduced pressure. The residue was dissolved in ethyl acetate, washed with saturated sodium chloride solution and dried with sodium sulfate. After removing the solvent, the residue was purified by silica gel-chromatography (chloroform) followed by crystallization from petroleum ether to give the desired compound. $^1$H-NMR(CDCl$_3$)δ 1.15(3H,t,NCH$_2$CH$_3$), 1.33(6H,d,CH(CH$_3$)$_2$), 2.79–2.86(4H,m,CH$_2$CH$_2$), 3.07(1H,septet,CH), 4.62(2H,q,NCH$_2$), 7.32–7.60(6H,m, Ar-H), 8.33(1H,d,H-8)

The following compounds have been synthesized in a manner analogous to Examples 7–9.

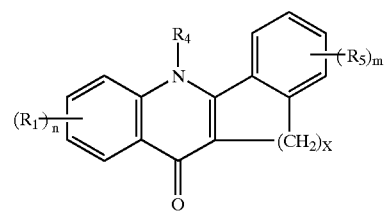

(XVIII)

The numbering of various substituents are those of respective fused ring systems, namely indeno[1,2-b]quinoline(x=1),benzo[c]acridine(x=2) and benzo[6,7]cyclohepta[1,2-b]quinoline, respectively.

TABLE III

| Compound No. | x | R$_4$ | R$_5$ | R$_1$ | |
|---|---|---|---|---|---|
| B1 | 1 | CH$_3$ | H | 8-i-C$_3$H$_7$ | 249(dec) |
| B2 | 1 | C$_2$H$_5$ | H | 8-i-C$_3$H$_7$ | 152–155 |
| B3 | 1 | Compound B2, HClsalt | | | 175–177 |
| B4 | 1 | C$_2$H$_5$ | H | 8-CH$_3$O | 205–207 |
| B5 | 1 | C$_2$H$_5$ | H | 6-F | 241–243 |
| B6 | 1 | CH$_3$ | H | 8-CH$_3$O 9-i-C$_3$H$_7$ | 297(dec) |
| B7 | 1 | C$_2$H$_5$ | H | 8-CH$_3$O 9-i-C$_3$H$_7$ | 217–218 |
| B8 | 1 | CH$_3$ | 2-C$_2$H$_5$ | 8-i-C$_3$H$_7$ | 220(dec) |
| B9 | 1 | C$_2$H$_5$ | 2-C$_2$H$_5$ | 8-i-C$_3$H$_7$ | 205 |
| B10 | 1 | C$_2$H$_5$ | 2-CH$_3$O | 8-i-C$_3$H$_7$ | 202–204 |
| B11 | 1 | CH$_3$ | 2-CH$_3$O | 8-i-C$_4$H$_9$ | 218 |
| B12 | 1 | C$_2$H$_5$ | 2-CH$_3$O | 8-i-C$_4$H$_9$ | 216–217 |
| B13 | 1 | CH$_3$ | 2-CH$_3$O | 8-i-C$_3$H$_7$ | 215–222 |
| B15 | 1 | C$_2$H$_5$ | 2-CH$_3$O | 8-i-C$_4$H$_9$ | 189–190 |
| B16 | 1 | CH$_3$ | 2-Cl | 8-i-C$_3$H$_7$ | 265(dec) |
| B17 | 1 | C$_2$H$_5$ | 2-Cl | 8-i-C$_3$H$_7$ | 186(dec) |
| B18 | 1 | CH$_3$ | 2-Br | 8-i-C$_3$H$_7$ | 280(dec) |
| B19 | 1 | C$_2$H$_5$ | 2-Br | 8-i-C$_3$H$_7$ | 225(dec) |
| B20 | 1 | C$_2$H$_5$ | 2-OCH$_3$ 3-CH$_3$ | 8-i-C$_3$H$_7$ | 217(dec) |
| B21 | 1 | CH$_3$ | 2,3-diCH$_3$O | 8-i-C$_3$H$_7$ | 253–254 |
| B22 | 1 | C$_2$H$_5$ | 2,3-diCH$_3$O | 8-i-C$_3$H$_7$ | 208 |
| B23 | 1 | C$_2$H$_5$ | 1,2-diCl | 8-i-C$_3$H$_7$ | 235(dec) |
| B24 | 2 | CH$_3$ | H | 9-i-C$_3$H$_7$ | 199–203 |
| B25 | 2 | C$_2$H$_5$ | H | 9-i-C$_3$H$_7$ | oil |
| B26 | 2 | CH$_3$ | H | 9-i-C$_4$H$_9$O | 160 |
| B27 | 2 | C$_2$H$_5$ | H | 9-i-C$_4$H$_9$O | 61 |
| B28 | 3 | CH$_3$ | H | 10-i-C$_3$H$_7$ | 167 |
| B29 | 1 | 4-FC$_6$H$_4$ | 2-CH$_3$O | 8-i-C$_3$H$_7$ | 285(dec) |
| B30 | 1 | 4-FC$_6$H$_4$ | 2-C$_2$H$_5$ | 8-i-C$_3$H$_7$ | 270(dec) |
| B31 | 1 | C$_6$H$_5$ | 2-CH$_3$O | 8-i-C$_3$H$_7$ | 208–210 |
| B32 | 1 | C$_2$H$_5$ | 2-CH$_3$O | 7-i-C$_3$H$_7$ 8-CH$_3$O | 224–225 |
| B33 | 1 | C$_2$H$_5$ | 2-C$_2$H$_5$ | 7-i-C$_3$H$_7$ 8-CH$_3$O | 210–212 |
| B34 | 1 | C$_2$H$_5$ | H | 7,9-diCH$_3$ 8-i-C$_4$H$_9$ | 184 |
| B35 | 1 | C$_2$H$_5$ | 2-CH$_3$O | 7,9-diCH$_3$ 8-i-C$_4$H$_9$ | 203–204 |
| B36 | 1 | C$_2$H$_5$ | 2-C$_2$H$_5$ | 7,9-diCH$_3$ 8-i-C$_4$H$_9$ | 140 |
| B37 | 1 | C$_2$H$_5$ | 1,3-diCH$_3$ 2-CH$_3$O | 8-i-C$_3$H$_7$ | 201 |
| B38 | 1 | 4-FC$_6$H$_4$ | 2-C$_2$H$_5$ | 7-i-C$_3$H$_7$ 8-CH$_3$O | 281(dec) |
| B39 | 1 | C$_2$H$_5$ | H | 8-i-C$_4$H$_9$O 9-CH$_3$ | 239–240 |

Part C.

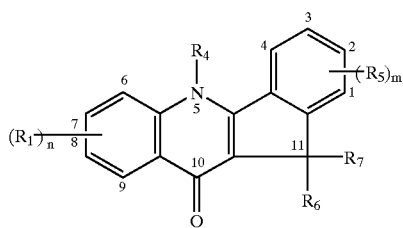

Example 10

5-Ethyl-8-isopropyl-5,10-dihydro-11H-indeno[1,2-b] quinolin-10,11-dione (Compound C47)

Under argon atmosphere, 60% sodium hydride (82 mg, 2.0 mmol) was added to a solution of 1,3-indandione (300 mg,2.0 mmol) in anhydrous DMF with ice cooling and stirring followed by stirring for additional 1 hour. To the mixture was added dropwise a solution of 1-ethyl-6-isopropylisatoic anhydride (238 mg,1.0 mmol) in anhydrous DMF followed by stirring at 60° C. for 3 hours. The reaction mixture was poured into ice-water. The resulting precipitate was filtered off, washed with water and dissolved in chloroform. The chloroform solution was washed with saturated sodium chloride solution and dried with sodium sulfate followed by evaporation to remove chloroform. The title compound was obtained by crystallizing from diethyl ether. $^1$H-NMR(CDCl$_3$)δ 1.30(6H,d,CH(CH$_3$)$_2$, 1.73(3H,t,NCH$_2$CH$_3$), 3.03(1H,septet,CH), 4.69($\overline{2H}$,q,NCH$_2$), 7.46–7.71($\overline{6H}$,m,Ar-H), 8.33(1H,s,H-9)

Example 11

5-Ethyl-8-isopropyl-11-hydroxyimino-5,10-dihydro-11H-indeno[1,2-b]quinolin-10-one (Compound C48)

5-Ethyl-8-isopropyl-5,10-dihydro-11H-indeno[1,2-b] quinolin-10,11-dione (300 mg, 0.95 mmol) was dissolved in a solution of hydroxylamine hydrochloride (525 mg, 7.6 mmol) and triethylamine (0.5 mL) in 20 mL of ethanol. The solution was refluxed overnight and then concentrated dryness. The residue was diluted with water and extracted with chloroform twice. The combined organic layers were washed with saturated sodium chloride solution, dried with sodium sulfate followed by evaporation to remove the solvent. The title compound was obtained by subjecting the resulting residue to silica gel-chromatography (chloroform:actone=20: 1) and then to crystallization from diethyl ether. $^1$H-NMR(CDCl$_3$)δ 1.32(6H,d,CH(CH$_3$)$_2$, 1.73(3H,t,NCH$_2$CH$_3$), 3.03(1H,septet,CH), 4.79($\overline{2H}$,q,NCH$_2$), 7.41–8.00($\overline{6H}$,m,Ar-H), 8.25(1H,s,H-9), 15.31(1H,s,N=OH)

Example 12

5-Ethyl-8-isopropyl-11-hydroxy-5,10-dihydro-11H-indeno[1,2-b]quinolin-10-one (Compound C43)

To an ethanolic solution of 5-ethyl-8-isopropyl-5,10-dihydro-11H-indeno[1,2-b]quinolin-10,11-dione (500 mg, 1,58 mmol) was added sodium borohydride (62 mg, 1.64 mmol) in portions followed by stirring at room temperature for 1 hour. After removing ethanol, the reaction mixture was diluted with water and extracted with chloroform twice. The combined organic layers were washed with saturated sodium chloride solution and dried with sodium sulfate followed by evaporating to remove chloroform. The title compound was obtained by crystallizing the residue from acetone-diethyl ether mixture. $^1$H-NMR(CDCl$_3$)δ 1.35(6H,d,CH(CH$_3$)$_2$), 1.72(3H,t,NCH$_2$CH$_3$), 3.11(1H,septet,CH), 4.79($\overline{2H}$,q,NCH$_2$), 5.86(1$\overline{H,s,H}$-11), 7.52–7.63(3H,m,Ar-H), 7.85(1H,dd,H-9)

Example 13

5-Ethyl-8-isopropyl-11-hydroxy-11-phenyl-5,10-dihydro-11H-indeno[1,2-b]quinolin-10-one (Compound C45)

2M solution of phenyl magnesium bromide in THF (1.07 mL, 1.87 mmol) was dissolved in anhydrous methylene chloride. To this solution was added dropwise a solution of 5-ethyl-8-isopropyl-5,10-dihydro-11H-indeno[1,2-b] quinolin-10,11-dione (500 mg, 1.58 mmol) in anhydrous methylene chloride with ice cooling and stirring followed by stirring at room temperature overnight. The reaction mixture was treated with 10% hydrochloric acid. The organic layer was separated, washed sequentially with diluted hydrochloric acid and saturated sodium chloride solution and dried with sodium sulfate followed by evaporation to remove methylene chloride. The title compound was isolated by subjecting the residue to silica gel-chromatography (chloroform) and crystallization from diethyl ether. $^1$H-NMR(CDCl$_3$)δ 1.30(6H,d,CH(CH$_3$)$_2$), 1,79(3H,t,NCH$_2$CH$_3$), 3.05(1H,septet,CH), 4.81($\overline{2H,q,N}$CH$_2$), 5.18(1H,s,H-$\overline{11}$), 7.16–7.64(10H,m,Ar-H), 7.96(1H,d,H-6), 8.37(1H,d,H-9)

Example 14

5-Ethyl-8-isopropyl-11-phenyl-5,10-dihydro-11H-indeno[1,2-b]quinolin-10-one (Compound C44)

To a mixture of trimethylsilyl chloride (0.19 mL, 1.5 mmol), sodium iodide (224 mg, 1.5 mmol) and acetonitrile (61 mg, 1.5 mmol) was added dropwise a solution of 5-ethyl-8-isopropyl-11-hydroxy-11-phenyl-5,10-dihydro-11H-indeno[1,2-b]quinolin-10-one in 1,2-dichloroethane with stirring at room temperature. The mixture was stirred at 50° C. overnight followed by allowing to cool to room temperature. The reaction mixture was treated diluted aqueous solution of sodium sulfite. The separated organic layer was washed with water four times and then with saturated sodium chloride solution followed by drying with sodium sulfate. After removing the solvent, the residue was purified by silica gel-chromatography (chloroform) followed by crystallization from diethyl ether to give the title compound. $^1$H-NMR(CDCl$_3$) δ 1.30(6H,d,CH(CH$_3$)$_2$), 1.79(3H,t,NCH$_2$CH$_3$), 3.05(1H,septet,CH), 4.81(2$\overline{H,q,N}$CH$_2$), 5.18(1H,s,H-$\overline{11}$), 7.16–7.64(10H,m,Ar-H), 7.96(1H,d,H-6), 8.37(1H,d,H-9)

Example 14

5-Ethyl-8-methoxy-9-methyl-5,10-dihydro-11H-indeno[1,2-b]quinolin-10,11-dione (Compound C60)

Step 1. 3-Methyl-4-methoxynitrobenzene

A solution of 2-fluoro-5-nitrotoluene (7.0 g, 45 mmol) in anhydrous DMF was added to a 28% methanolic solution of sodium methoxide (10.45 g, 54 mmol) under ice-cooling with stirring. The reaction mixture was stirred at room temperature overnight and then poured into ice water. The resulting precipitate was filtered off and dissolved in diethyl ether. This solution was washed with saturated sodium chloride solution, dried with sodium sulfate and evaporated to dryness to give the desired compound. $^1$H-NMR(CDCl$_3$)δ 2,27(3H,s,CH$_3$), 3.94(3H,s,OCH$_3$), 6.87(1H,d,H-5), 8.03(1H,d,H-2), 8.11(1H,dd,H-6)

Step 2. 2-Bromo-4-methoxy-5-methylaniline

To a solution of 3-methyl-4-methoxynitrobenzene(7.59 g, 45 mmol) in ethanol was added iron powder (35 g), water(5 mL) and concentrated hydrochloric acid (0.4 mL). The mixture was refluxed for 1 hour and then filtered while hot. The filtrate was concentrated to dryness. The residue was dissolved in chloroform. The chloroform solution was dried with sodium sulfated and evaporated to give 3-methyl-4- methoxyaniline (7.59 g). To a solution of this compound (6.17 g, 45 mmol) in acetic acid (55 mL) were added dropwise acetic anhydride (4,4 mL, 46 mmol) at room temperature with stirring and then bromine(2,4 mL, 46 mmol) at 50° C. with stirring. The reaction mixture was stirred at the same temperature for 2 hours and poured into ice-water. The resulting precipitate was filtered off, washed with water and dissolved in ethyl acetate. This solution was washed with saturated sodium chloride solution, dried with sodium sulfate and evaporated to dryness to give 2-bromo-4-methoxy-5-methylacetanilide as a crude product. Crystallization from diethyl ether gave pure product (8.27 g).

This product was dissolved in ethanol and concentrated hydrochoric acid (26 mL) was added thereto. The mixture was refluxed for 2 hours and then concentrated to dryness. The residue was made weak alkaline with sodium hydroxide. The resulting precipitate was filtered off, washed with water and dried under reduced pressure to give the desired compound. $^1$H-NMR(CDCl$_3$)δ 2.11(3H,s,CH$_3$), 3,74(3H,s,OCH$_3$), 3.74(2H,m,NH$_2$), 6.61(1H,d,Ar-H), 6.87(1H,s,Ar-H)

Step 3. 5-Methyl-6-methoxy-8-bromoisatoic anhydride

The title compound was prepared from 2-bromo-4-methoxy-5-methylaniline via 4-methyl-5-methoxy-7-bromoisatin in a manner analogous to that described in Example 5.

Step 4. 1-Ethyl-5-methyl-6-methoxyisatoic anhydride 5-methyl-6-methoxy-8-bromoisatoic anhydride (1,39 g, 4.8 mmol) in DMF was hydrogenated in the presence of 5% Pd-C overnight. After filtering, the reaction mixture was concentrated to dryness and dissolved in ethyl acetate. This solution was washed with saturated sodium chloride solution, dried with sodium sulfate and evaporated to dryness to give 5-methyl-6-methoxyisatoic anhydride.

Reaction of this compound with ethyl iodide in the presence of sodium hydride gave the title compound.

Step 5. 5-Ethyl-8-methoxy-9-methyl-5,10-dihydro-11H-indeno[1,2-b]quinolin-10,11-dione 1-Ethyl-5-methyl-6-methoxyisatoic anhydride was reacted with 1,3-indandione as in Example 10 to give the desired compound. $^1$H-NMR(CDCl$_3$) δ 1.70(3H,t,NCH$_2$CH$_3$), 2.83(3H,s,CH$_3$), 3.88(3H,s,OCH$_3$), 4.64(2H,q,NCH$_2$), 7.18–7.69(6H,m,Ar-H)

Example 15

5-Ethyl-8-isobutoxy-9-methyl-5,10-dihydro-11H-indeno[1,2-b]quinolin-10,11-dione (Compound C61)

To a solution of boron tribromide (0.3 mL, 3,3 mmol) in methylene chloride was added dropwise a solution of 5-ethyl-8-methoxy-9-methyl-5,10-dihydro-11H-indeno[1,2-b]quinolin-10,11-dione(325 mg, 1.0 mmol) in methylene chloride under ice cooling with stirring followed by stirring at room temperature overnight. The reaction mixture was poured into a 10% aqueous solution of sodium hydroxide. The aqueous layer was acidified with hydrochloric acid to yield a precipitate. This precipitate was filtered off, washed with water and dried under reduced pressure to give the corresponding 8-hydroxy compound (331 mmg, 100%). This product (331 mg, 1.0 mmol) was dissolved in anhydrous DMF and 60% sodium hydride (48 mg, 1.2 mmol) was added thereto at room teperature with stirring. After stirring for 1 hour, the reaction mixture was allowed to react with isobutyl bromide (0.1 mL, 1.5 mmol) added thereto at 60° C. overnight with stirring. The reaction mixture was concentrated to dryness and the residue was dissolved in chloroform. The chloroform solution was washed with saturated sodium chloride solution, dried with sodium sulfate and evaporated to dryness. The residue was purifie by silica gel-chromatography (chloroform:methanol=30:1) to obtain the desired compound. $^1$H-NMR(CDCl$_3$)δ 1.08(6H,d,OCH$_2$CH(CH$_3$)$_2$), 1.67(3H,t,NCH$_2$CH$_3$), 2.13(1H,m,OCH$_2$CH(CH$_3$)$_2$), 2.80(3H,s,CH$_3$), 3.72(2H,d,OCH$_2$CH(CH$_3$)$_2$), 4.64(2H,q,NCH$_2$), 7.10–7.63(6H,m,Ar-H)

Example 16

5-Ethyl-8-isobutoxy-9-methyl-11-hydroxy-5,10-dihydro-11H-indeno[1,2-b]quinolin-10-one (Compound C62)

5-Ethyl-8-isobutoxy-9-methyl-5,10-dihydro-11H-indeno[1,2-b]quinolin-10,11-dione was treated as in Example 12 to give the title compound. $^1$H-NMR(CDCl$_3$) δ 1.10(6H,d,OCH$_2$CH(CH$_3$)$_2$), 1.69(3H,t,NCH$_2$CH$_3$), 2.17(1H,m,OCH$_2$CH(CH$_3$)$_2$), 3.00(3H,s,CH$_3$), 3,81(2H,d,OCH$_2$CH(CH$_3$)$_2$), 4.31(1H,s,H-11), 4.65(2H,q,NCH$_2$), 5,80(1H,s,OH), 7.28–7.74(6H,m,Ar-H)

Starting from 5-ethyl-8-isopropyl-5,10-dihydro-11H-indeno[1,2-b]quinolin-10,11-dione (Compound C47), the following compound have been prepared using known methodology.

5-Ethyl-8-isopropyl-11-methyl-5,10-dihydro-11H-indeno[1,2-b]quinolin-10-one (Compound C40) mp 152–154;

5-Ethyl-8-isopropyl-11-amino-5,10-dihydro-11H-indeno[1,2-b]quinolin-10-one dihydrochloride (Compound C41), mp 200° C. (decomp);

5-Ethyl-8-isoproypl-11-methoxyimino-5,10-dihydro-11H-indeno[1,2-b]quinolin-10-one (Compound C49) mp 150° C.;

5-Ethyl-8-isopropyl-11-acetylamino-5,10-dihydro-11H-indeno[1,2-b]quinolin-10-one (Compound C42), mp215° C. (decomp); and 5-Ethyl-8-isopropyl-11-methoxy-11-phenyl-5,10-dihydro-11H-indeno[1,2-b]quinolin-10-one, (Compound C46), mp 237–239.

Part D.

(I-f)

(I-g)

Example 17

10-Ethyl-7-isopropyl-2-methyl-5,10-dihydro-4H-thieno[3',2':4,5]cyclopenta[1,2-b]quinolin-5-one (Compound D51)

Step 1. 3-Chloro-1-(5-methyl-2-thienyl)-1-propanone

To a suspension of anhydrous aluminum chloride (4 g,0.03 mol) in nitrobenzene (10 mL) was added dropwise a solution of 2-methylthiophene (2.0 g, 0.02 mol) and 3-chloropropionyl chloride (3.8 g, 0.20 mol) in nitrobenzene (10 mL). After stirring for 3 hours, the reaction mixture was poured into ice-water (200 mL) containing concentrated hydrochloric acid (20 mL) followed by extraction with diethyl ether. The orgaic layer was sequentially washed with water and saturated sodium chloride solution dried with sodium sulfate and evaporated to remove diethyl ether. The residue was further evaporated under reduced pressure to remove nitrobenzene and purified by silica gel-chromatography (hexane:ethyl acetate=19:1) to give the desired compound (2.5 g, 66.2%). $^1$H-NMR(CDCl$_3$) δ 2.54 (3H,s,CH$_3$), 3.32(2H,t,CH$_2$Cl), 3,89(2H,t,COCH$_2$), 6.81–6.83(1H,m,H-4), 7.56(1H,d,H-3)

Step 2. 2-Methyl-4,5-dihydro-6H-cyclopenta[b]thiophen-6-one

3-Chloro-1-(5-methyl-2-thienyl)-1-propanone (2,5 g,13.2 mmol) was heated in concentrated sulfuric acid (20 mL) at 100° C. for 50 minutes with stirring. The reaction mixture was gradually poured into ice-water (200 g) and extracted with diethyl ether. The organic layer was sequnetially washed with water and saturated sodium chloride solution, dried with sodium sulfate and evaporated to dryness. The residue was purified by silica gel-chromatography (chloroform) to give the desired compound. $^1$H-NMR (CDCl$_3$) δ 2.57(3H,s,CH$_3$), 2.87–2.97(4H,m,COCH$_2$CH$_2$), 6.75(1H,s,H-3)

Step 3. 10-Ethyl-7-isopropyl-2-methyl-5,10-dihydro-4H-thieno[3',2':4,5]cyclopenta[1,2-b]quinolin-5-one To a 1.53M solution of n-butyl lithium in hexane (0.47 mL, 0.72 mmol) were added under argon atmosphere TMEDA (0.11 mL, 0.72 mmol) at room temperature and then 2-methyl-4,5-dihydro-6H-cyclopenta[b]thiophen-6-one (0.11 g, 0.72 mmol) in anhydrous THF dropwise with ice cooling and stirring. The reaction mixture was stirred at room temperature for 1 hour and ice-cooled again. To this was added dropwise a solution of 1-ethyl-6-isopropylisatoic anhydride (Example 6, step 1) (0.11 g, 0.48 mmol) in anhydrous THF. The reaction mixture was stirred at room temperature for 2 hours and diluted with saturated aqueous solution of ammonium chloride. The organic layer was concentrated to dryness and the residue was dissolved in ethyl acetate. This solution was washed with saturated sodium chloride solution, dried with sodium sulfate and evaporated again. The residue was subjected to silica gel-chromatography (chloroform: acetone=9:1) and crystallization from diethyl ether to give the title compound. $^1$H-NMR (CDCl$_3$) δ 1.33(6H,d,CH(CH$_3$)$_2$), 1.58(3H,t,CH$_2$CH$_3$), 2.64 (3H,s,CH$_3$), 3.10(1H,septet,CH), 3,78(2H,s,H-4), 4,49(2H, q,NCH$_3$), 6.97(1H,s,H-3), 7.49(1H,d,H-9), 7.56(1H,dd,H-8), 8.45(1H,d,H-6)

The following compounds have been synthesized in a manner analogous to that described in Example 17.

10-Ethyl-7-isopropyl-5,10-dihydro-4H-thieno[3',2': 4,5]cyclopenta[1,2-b]quinolin-5-one (Compound D50), mp 168–169° C.;

10-Ethyl-7-isopropyl-3-methyl-5,10-dihydro-4H-thieno[3',2':4,5]cyclopenta[1,2-b]quinolin-5-one (compound D52), mp 195° C. (decomp); and 4-Ethyl-7-isopropyl-1-methyl-4,9-dihydro-10H-pyrrolo[2',3':4,5]cyclopenta[1,2-b]quinolin-9-one (Compound D53), mp 91–93° C.

BIOLOGICAL EXAMPLES

1. In vitro anti-picornavirus activity

Poliovirus type 1 (Polio 1, Sabin), echovirus type 11 (Echo 11, Gregory), coxsackievirus type A7 (CA7), coxsackievirus type B4 (CB4,JVB), human rhinovirus type 1B (HRV 1B, B632), HRV 2 (HGP), and HRV 89 (41617-Gallo) were used. Polio 1, Echo 11, and CA7 were assayed in HeLa-S3 cells with the exception of the CB4, which were assayed in HeLa cells; all numbered HRV serotypes were assayed in HeLa (Ohio strain) cells. Cells were seeded at 2.0×10$^4$ cells/well (in Eagle MEM plus 7% fetal bovine serum, growth medium) in 96-well tissue culture plate and were incubated for 24 hr. at 37° C. in a CO$_2$ incubator to form monolayer. The growth medium in the plates was removed and a serial 0.5 log$_{10}$ dilutions of the test compound in 50 μl maintenance medium (Eagle MEM plus 2% heat-inactivated fetal bovine serum) was added to the wells. Each drug concentration was run in quadruplicate. Immediately after addition of compounds, the cells in 96-well plate were infected with appropriate virus at 300–1,000 plaque forming units (PFU) per well in 50μl of maintenance medium and were incubated at 33° C. for HRVs or 37° C. for enteroviruses. Uninfected cells and cells that received virus in the absence of compound were included on each plate. The anti-picornavirus activities of the compounds were examined by calorimetric assay based on the cells as monitored by reduction of 3-(4,5-dimethyl-2-thiazolyl)-2,5-diphenyl-2H-tetrazolium bromide (MTT) to formazan. After 3–5 days, 20 μl of MTT solution (4 mg/ml) in phosphate buffered saline (PBS) was added to each well, and the incubation was continued for an additional 2.5–4 hr. After incubation, 100 μl of 15% SDS in 0.01N HCl was added to each well to solubilize the bluish violet crystal of formazan and the plates were incubated at 37° C. for an additional 18 hr. The absorbency of formazan at 600 nm with a reference wave length of 660 nm was measured by a computer-controlled microplate reader. The 50% inhibitory concentration (IC$_{50}$) by the MTT method was defined as the concentration of compound that protected 50% of the cell monolayer from virus-induced cytopathic effect. The percentage protection was calculated by the following equation: $[(A_T)v\text{-}(Ac) v/(Ac)_{m\ o\ c\ k}\text{-}(Ac)v]\times 100\%$, where $(A_T)V$, (Ac) v, $(Ac)_{m\ o\ c\ k}$ indicate absorbencies of the test sample, the virus-infected control (no compound) and mock-infected control, respectively.

The cytotoxicity of the compound was determined as described above without inoculation of the virus and expressed as the 50% cytotoxic concentration (CC$_{50}$), i.e., the concentration required to reduce the viability of untreated cells by 50%. The cells were exposed to various concentrations of the test compounds in the maintenance medium and incubated for 4 days.

A majority of the compounds of the present invention exhibited anti-picornavirus activities as shown in table IV–VI.

TABLE IV in vitro Anti-picornavirus activity

| Compound | IC$_{50}$ (μg/ml) | | | | | | |
|---|---|---|---|---|---|---|---|
| | Polio 1 | Echo 11 | CA7 | CB4 | HRV1B | HRV2 | HRV89 |
| A30 | 1.0 | 0.42 | 1.2 | 1.8 | 1.6 | 0.48 | 1.0 |
| A32 | 0.93 | 0.40 | 1.9 | >3.3 | 1.0 | 0.55 | 0.77 |
| A37 | 1.1 | 0.91 | 3.8 | 6.7 | 1.0 | 0.83 | 0.54 |
| A60 | 1.1 | 0.52 | 2.5 | 2.8 | 0.59 | 0.52 | 1.1 |
| A61 | 0.73 | 0.40 | >4 | >4 | 0.64 | 0.65 | 0.38 |
| A78 | 1.3 | 1.2 | 7.1 | 2.6 | 5.6 | 1.7 | 2.9 |
| A81 | 0.78 | 0.52 | 0.78 | 2.2 | 1.7 | 0.86 | 0.55 |
| A97 | 0.54 | 0.3 | 2.1 | 1.4 | 0.58 | 0.61 | 0.14 |
| A98 | 0.66 | 0.26 | 2.9 | 1.2 | 0.78 | 0.42 | 0.36 |
| A99 | 0.55 | 0.20 | 1.8 | 1.1 | 0.63 | 0.50 | 0.14 |
| A100 | 0.57 | 0.24 | 4.5 | 1.4 | 0.85 | 0.43 | 0.20 |
| A122 | 1.2 | 0.54 | 6.9 | 5.5 | 0.59 | 0.43 | 0.35 |
| A130 | 0.86 | 0.32 | 0.17 | >4 | 0.90 | 0.65 | 0.72 |
| A157 | 0.59 | 0.27 | 3.8 | 4.9 | 1.0 | 0.56 | 1.3 |
| A159 | 0.51 | 0.26 | 2.7 | 3.0 | 0.78 | 0.48 | 0.73 |
| A160 | 0.55 | 0.27 | 2.7 | 2.9 | 0.73 | 0.45 | 0.78 |
| A169 | 4.3 | 1.1 | >50 | 18 | 8.2 | 1.0 | 5.4 |
| A171 | 0.52 | 0.22 | 1.9 | 2.0 | 0.43 | 0.76 | 0.39 |
| A179 | 0.29 | 0.20 | 2.4 | 1.2 | 0.86 | 0.87 | 0.37 |

TABLE IV-continued in vitro Anti-picornavirus activity

| Compound | IC$_{50}$ (μg/ml) | | | | | | |
|---|---|---|---|---|---|---|---|
| | Polio 1 | Echo 11 | CA7 | CB4 | HRV1B | HRV2 | HRV89 |
| A181 | 0.39 | 0.24 | 2.4 | 1.8 | 1.6 | 0.94 | 0.46 |
| A186 | 0.67 | 0.27 | 3.0 | 1.2 | 1.1 | >1.7 | 0.26 |
| A187 | 0.53 | 0.21 | 3.0 | 0.99 | 0.71 | 0.57 | 0.15 |
| A188 | 0.31 | 0.27 | 1.2 | 1.1 | 0.81 | 0.33 | 0.25 |
| A190 | 0.58 | 0.23 | 3.2 | 2.4 | 2.0 | 0.57 | 0.28 |
| A191 | 0.40 | 0.19 | 2.5 | 1.6 | 1.3 | 0.15 | 0.20 |
| A194 | 0.58 | 0.45 | 1.7 | 1.3 | 0.05 | 0.49 | 0.18 |
| A196 | 1.1 | 0.44 | 9.7 | 1.9 | 5.9 | 1.8 | 0.86 |
| A226 | 0.93 | 0.33 | 9.7 | >3.3 | 1.6 | 0.73 | <0.033 |
| A234 | 0.89 | 0.25 | 3.8 | 2.5 | 1.0 | 0.26 | 0.32 |
| A235 | 0.72 | 0.27 | 2.8 | 2.9 | 0.75 | 0.24 | 0.35 |
| A237 | 1.1 | 0.40 | >4 | 2.9 | 2.0 | 0.29 | 0.46 |
| A258 | 0.62 | 0.23 | 4.9 | >1.6 | 0.62 | 0.45 | 0.66 |
| A285 | 0.69 | 0.2 | 3.1 | 1.9 | 0.68 | 0.18 | 0.46 |
| A286 | 1.3 | 0.57 | >5 | 1.4 | 0.87 | 0.23 | 0.61 |
| A296 | 5.1 | 1.7 | 20 | 17 | 4.5 | 2.0 | 4.8 |
| A303 | 1.4 | 0.83 | 6.5 | 3.6 | 1.4 | 0.97 | 1.9 |
| A304 | 0.80 | 0.35 | 3.6 | 1.9 | 0.76 | 0.34 | 0.90 |
| A306 | 0.83 | 0.49 | 2.9 | 2.1 | 0.89 | 0.73 | 0.88 |
| A307 | 0.79 | 0.34 | 1.9 | 1.3 | 0.83 | 0.39 | 0.86 |
| A308 | 0.87 | 0.31 | 3.9 | 1.6 | 0.81 | 0.36 | 0.94 |
| A309 | 0.76 | 0.28 | 3.3 | 1.5 | 0.48 | 0.25 | 0.58 |
| A311 | 0.67 | 0.42 | 3.3 | 2.0 | 1.0 | 0.53 | 1.2 |
| A313 | 0.94 | 0.35 | 3.8 | 3.0 | 0.90 | 0.33 | 0.96 |
| A314 | 0.60 | 0.51 | 1.5 | 0.82 | 0.56 | 0.55 | 0.38 |
| A315 | 0.54 | 0.30 | 1.2 | 0.63 | 0.52 | 0.28 | 0.26 |
| A316 | 0.78 | 0.39 | 1.2 | 1.1 | 0.56 | 0.29 | 0.27 |
| A317 | 0.81 | 0.35 | 2.6 | 1.1 | 0.82 | 0.43 | 0.40 |
| A318 | 0.47 | 0.27 | 2.0 | 0.65 | 0.45 | 0.38 | 0.16 |
| A319 | 2.0 | 0.81 | 8.9 | 9.4 | 1.5 | 0.80 | 2.0 |
| A320 | >5 | 0.15 | >5 | >5 | 0.12 | 0.051 | 0.051 |
| A321 | NT | NT | NT | NT | 0.60 | 0.056 | 0.066 |
| A322 | NT | NT | NT | NT | 0.18 | 0.030 | 0.034 |
| A323 | >2 | >2 | >2 | >2 | 0.27 | 0.038 | 0.011 |
| A324 | NT | NT | NT | NT | 0.53 | 0.12 | 0.046 |
| A325 | >2.5 | >2.5 | >2.5 | >2.5 | >2.5 | 0.066 | 0.022 |
| A326 | >2.5 | >2.5 | >2.5 | >2.5 | >2.5 | 0.48 | 0.067 |

TABLE V-1 in vitro Anti-picornavirus activity

| Compd. | IC$_{50}$ (μg/ml) | | | | | | | | |
|---|---|---|---|---|---|---|---|---|---|
| | polio 1 | Echo 11 | CA7 | CB4 | HRV 1A | HRV 1B | HRV 2 | HRV 14 | HRV 89 |
| B2 | 0.58 | 0.19 | 3.1 | 0.97 | 5.0 | 0.54 | 0.15 | 0.65 | 0.48 |
| B3 | 0.72 | 0.35 | 2.1 | 0.82 | 2.6 | 0.30 | 0.54 | 0.74 | 0.57 |
| B7 | 0.42 | 0.25 | 1.4 | 0.52 | 1.7 | 0.17 | 0.36 | 0.49 | 0.30 |
| B8 | 0.19 | 0.17 | 0.70 | 0.60 | >1 | 0.24 | 0.22 | 0.40 | 0.12 |
| B9 | 0.18 | 0.18 | 0.71 | 0.56 | >1 | 0.25 | 0.20 | 0.58 | 0.21 |
| B10 | 0.17 | 0.14 | 1.4 | 0.57 | 1.9 | 0.25 | 0.16 | 0.52 | 0.33 |
| B11 | 0.45 | 0.28 | >2 | 1.6 | 1.7 | 0.36 | 0.34 | 0.78 | 0.31 |
| B12 | 0.39 | 0.19 | 2.0 | 0.63 | >2.5 | 0.25 | 0.31 | 0.43 | 0.31 |
| B15 | 0.49 | 0.27 | 2.2 | 1.9 | >2.5 | 0.36 | 0.44 | 0.84 | 0.39 |
| B20 | 0.40 | 0.28 | 1.4 | 0.60 | >2.5 | 0.23 | 0.19 | 0.51 | 0.18 |
| B22 | 0.54 | 0.39 | 1.9 | 1.3 | >5.9 | 0.44 | 0.55 | 0.86 | 0.36 |

TABLE V-2 in vitro Anti-picornavirus activity

| Compd. | IC$_{50}$ (μg/ml) | | | | | | | | |
|---|---|---|---|---|---|---|---|---|---|
| | polio 1 | Echo 11 | CA7 | CB4 | HRV 1A | HRV 1B | HRV 2 | HRV 14 | HRV 89 |
| C40 | 0.54 | 0.24 | >3.3 | 1.7 | >3.3 | 0.51 | 0.54 | 1.1 | 0.56 |
| C43 | 1.5 | 0.54 | >5 | 2.9 | >5 | 1.5 | 0.67 | 2.5 | 0.86 |
| C49 | 0.52 | 0.26 | 9.2 | 2.3 | >10 | 1.9 | 1.7 | 5.5 | 2.1 |

TABLE V-3 in vitro Anti-picornavirus activity

| Compd. | IC$_{50}$ (μg/ml) | | | | | | | | |
|---|---|---|---|---|---|---|---|---|---|
| | polio 1 | Echo 11 | CA7 | CB4 | HRV 1A | HRV 1B | HRV 2 | HRV 14 | HRV 89 |
| D50 | 0.64 | 0.27 | 1.9 | 0.82 | 2.2 | 0.25 | 0.20 | 1.3 | 0.41 |
| D51 | 0.28 | 0.21 | 1.1 | 0.72 | 3.1 | 0.59 | 0.27 | 0.82 | 0.35 |
| D52 | 1.0 | 0.55 | >5 | 3.0 | 3.1 | 0.89 | 0.86 | 1.1 | 0.85 |
| D53 | 1.8 | 0.68 | >10 | >3.3 | >10 | 1.6 | 0.91 | 2.3 | 1.4 |

TABLE VI-1

Cytotoxicity

| Compound | CC$_{50}$(μg/ml) | | |
|---|---|---|---|
| | HeLa-S3 | HeLa | HeLa(Ohio) |
| A 30 | 6.5 | 6.0 | 5.8 |
| A 32 | >10 | 9.7 | >10 |
| A 37 | 12 | 11 | 11 |
| A 60 | 7.0 | 5.3 | 5.7 |
| A 61 | >4 | >4 | >4 |
| A 78 | >8 | >8 | >8 |
| A 81 | 7.6 | 6.5 | 5.8 |
| A 97 | >10 | 5.1 | 4.5 |
| A 98 | >4 | >4 | >4 |
| A 99 | 5.8 | 5.4 | 5.7 |
| A100 | >5 | >5 | >5 |
| A122 | >10 | >10 | >10 |
| A130 | >4 | >4 | >4 |
| A157 | >5 | >5 | >5 |
| A159 | >5 | >5 | >5 |
| A160 | >5 | >5 | >5 |
| A169 | >50 | >50 | >50 |
| A171 | >2.5 | >2.5 | >2.5 |
| A179 | >4 | >4 | >4 |
| A181 | >2.5 | >2.5 | >2.5 |
| A186 | >5 | >5 | 5.0 |
| A187 | >4 | >4 | >4 |
| A188 | >5 | >5 | >5 |
| A190 | >4 | >4 | >4 |
| A191 | >4 | >4 | >4 |
| A194 | >2.5 | >2.5 | >2.5 |
| A196 | >10 | >10 | >10 |
| A226 | >10 | >10 | >10 |
| A234 | >5 | >5 | >5 |
| A235 | >4 | >4 | >4 |
| A237 | >4 | >4 | >4 |
| A258 | >5 | 4.5 | 4.9 |
| A285 | >4 | >4 | >4 |
| A286 | >5 | >5 | >5 |
| A296 | >100 | 75 | 68 |
| A303 | >20 | >20 | >20 |
| A304 | >20 | 18 | 19 |
| A306 | 26 | 14 | 25 |
| A307 | >20 | >20 | 18 |
| A308 | 16 | 11 | 11 |
| A309 | 18 | 12 | 14 |

TABLE VI-1-continued

Cytotoxicity

| Compound | CC$_{50}$(μg/ml) HeLa-S3 | HeLa | HeLa(Ohio) |
|---|---|---|---|
| A311 | >10 | 6.8 | >10 |
| A313 | >20 | 18 | 15 |
| A314 | >10 | 7.0 | >10 |
| A315 | >10 | 7.1 | >10 |
| A316 | >5 | >5 | >5 |
| A317 | >5 | >5 | >5 |
| A318 | >2.5 | >2.5 | >2.5 |
| A319 | >50 | 35 | 32 |
| A320 | >5 | >5 | >5 |
| A321 | NT | NT | >1 |
| A322 | NT | NT | >1 |
| A323 | >2 | >2 | >2 |
| A324 | NT | NT | >1 |
| A325 | >2.5 | >2.5 | >2.5 |
| A326 | >2.5 | >2.5 | >2.5 |

TABLE VI-2

Cytotoxicity

| Compound | CC$_{50}$(μg/ml) HeLa-S3 | Hela | HeLa(Ohio) |
|---|---|---|---|
| B 2 | >10 | >10 | >10 |
| B 3 | >4 | >4 | >4 |
| B 7 | >2.5 | >2.5 | >2.5 |
| B 8 | >1 | >1 | >1 |
| B 9 | >1 | >1 | >1 |
| B10 | >2.5 | >2.5 | >2.5 |
| B11 | >2 | >2 | >2 |
| B12 | >2.5 | >2.5 | >2.5 |
| B15 | >2.5 | >2.5 | >2.5 |
| B20 | >2.5 | >2.5 | >2.5 |
| B22 | >10 | >10 | >10 |

TABLE VI-3

Cytotoxicity

| Compound | CC$_{50}$(μg/ml) HeLa-S3 | HeLa | HeLa(Ohio) |
|---|---|---|---|
| D50 | >10 | 7.8 | >10 |
| D51 | >5 | >5 | >5 |
| D52 | >5 | >5 | >5 |
| D53 | >10 | >10 | >10 |

2. Anti-rhinovirus spectrum

In the above cell-based assays, some compounds demonstrate potent antiviral activities against 3 HRV serotypes tested. Therefore, we expanded our assessment of the antiviral activity of the compounds to a larger panel of HRV serotypes. HRV1A (E28), HRV3(FEB), HRV50, HRV8 (MRH), HRV10(204-CV14), HRV13(353), HRV14(1059), HRV16(11757), HRV21(47), HRV29(5582), HRV31(41F), HRV32(363), HRV33(1200), HRV36(342H), HRV39(209), HRV41(56110), HRV50(A2#58), HRV61(6669-CV39), and clinical isolate (89229T) were tested in the same method described above for sensitivity to the compounds. As shown in Table VII and VIII, some of the compounds exhibit potent activity against a broad spectrum of rhinovirus serotypes.

TABLE VII

Anti-rhinovirus activity

| Rhinovirus Serotype | Compd. A320 | Compd. A322 | Compd. A323 |
|---|---|---|---|
| HRV1A | >5.0 | >1.0 | >2.0 |
| HRV1B | 0.12 | 0.18 | 0.27 |
| HRV2 | 0.051 | 0.030 | 0.038 |
| HRV3 | >5.0 | >1.0 | >2.0 |
| HRV5 | >5.0 | >1.0 | >2.0 |
| HRV8 | >5.0 | >1.0 | >2.0 |
| HRV10 | >0.021 | 0.013 | 0.032 |
| HRV13 | 0.23 | 0.029 | 0.12 |
| HRV14 | >5.0 | >1.0 | >2.0 |
| HRV16 | 0.023 | 0.030 | 0.033 |
| HRV21 | 0.024 | 0.048 | 0.067 |
| HRV29 | 0.079 | 0.080 | 0.11 |
| HRV31 | 0.046 | 0.045 | 0.088 |
| HRV32 | 0.051 | 0.020 | 0.077 |
| HRV33 | 0.23 | 0.17 | 0.030 |
| HRV36 | 0.082 | 0.085 | 0.13 |
| HRV39 | <0.017 | 0.012 | 0.018 |
| HRV41 | 0.066 | 0.034 | 0.058 |
| HRV50 | 0.020 | 0.023 | 0.038 |
| HRV61 | 0.21 | 0.29 | 0.30 |
| HRV89 | 0.051 | 0.034 | 0.011 |
| Clinically isolated strain | 0.017 | 0.017 | 0.030 |

TABLE VIII

Anti-Rhinovirus activity

| Virus | Compd. B3 | Compd. B7 | Compd. B9 | Compd. B10 | Compd. B12 | Compd. B15 | Compd. B20 | Compd. B22 |
|---|---|---|---|---|---|---|---|---|
| HRV1A | 2.6 | 1.7 | >1.0 | 1.9 | >2.5 | >2.5 | >2.5 | >5.9 |
| HRV1B | 0.30 | 0.20 | 0.25 | 0.25 | 0.25 | 0.36 | 0.23 | 0.44 |
| HRV2 | 0.54 | 0.36 | 0.20 | 0.16 | 0.31 | 0.44 | 0.19 | 0.50 |
| HRV3 | 2.9 | 0.49 | 0.23 | 0.48 | 0.52 | 1.1 | 0.50 | 0.97 |

TABLE VIII-continued

Anti-Rhinovirus activity

| Virus | Compd. B3 | Compd. B7 | Compd. B9 | Compd. B10 | Compd. B12 | Compd. B15 | Compd. B20 | Compd. B22 |
|---|---|---|---|---|---|---|---|---|
| HRV5 | 0.36 | 0.22 | 0.17 | 0.24 | 0.29 | 0.39 | 0.23 | 0.43 |
| HRV8 | 0.46 | 0.32 | 0.15 | 0.20 | 0.32 | 0.38 | 0.29 | 0.46 |
| HRV10 | 1.8 | 0.41 | 0.47 | 0.41 | 0.43 | 1.1 | 0.42 | 0.53 |
| HRV13 | 0.17 | 0.13 | 0.14 | 0.12 | 0.091 | 0.18 | 0.13 | 0.13 |
| HRV14 | 0.74 | 0.49 | 0.58 | 0.52 | 0.43 | 0.84 | 0.51 | 0.86 |
| HRV16 | 2.3 | 0.98 | 0.47 | 0.57 | 1.4 | 1.2 | 0.44 | 1.2 |
| HRV21 | 0.20 | 0.11 | 0.16 | 0.16 | 0.17 | 0.34 | 0.14 | 0.18 |
| HRV29 | 1.5 | 0.43 | 0.19 | 0.44 | 0.44 | 0.67 | 0.44 | 0.56 |
| HRV31 | 0.29 | 0.13 | 0.15 | 0.15 | 0.11 | 0.38 | 0.18 | 0.14 |
| HRV32 | 0.61 | 0.30 | 0.13 | 0.36 | 0.33 | 0.65 | 0.29 | 0.19 |
| HRV33 | 0.20 | 0.097 | 0.094 | 0.11 | 0.12 | 0.29 | 0.097 | 0.16 |
| HRV36 | 0.30 | 0.16 | 0.16 | 0.17 | 0.21 | 0.32 | 0.20 | 0.25 |
| HRV39 | 1.7 | 0.38 | 0.20 | 0.39 | 0.38 | 0.46 | 0.35 | 0.46 |
| HRV41 | 0.20 | 0.064 | 0.13 | 0.007 | 0.11 | 0.18 | 0.12 | 0.14 |
| HRV50 | 0.20 | 0.12 | 0.13 | 0.10 | 0.12 | 0.28 | 0.18 | 0.17 |
| HRV61 | 0.80 | 0.28 | 0.16 | 0.24 | 0.31 | 0.39 | 0.31 | 0.34 |
| HRV89 | 0.57 | 0.30 | 0.21 | 0.33 | 0.31 | 0.39 | 0.18 | 0.36 |
| Clinical isolated strain | 1.9 | 0.50 | 0.31 | 0.75 | 0.46 | 1.1 | 0.49 | 0.43 |

3. In vitro anti-Rotavirus activity

Human rotavirus (HROV, Odelia) and simian rotavirus (SRoV, SA11) were used in this experiment. Confluent monolayers of MA104 cells in 6-well multiplate were washed with Eagle MEM containing 0.5 μg/ml of trypsin and were infected with tripsinized-rotavirus (treated with 10 μg/ml of tripsin at 37° C. for 1.5 hr) at 50 PFU per well. After 1 hr of adsorption, the virus inoculum was removed, and the monolayers were washed with Eagle MEM containing 0.5 μg/ml of trypsin and overlaid with Eagle MEM containing 1 μg/ml of trypsin, 0.6% purified agar and the test compounds at various concentrations. The cultures were incubated at 37° C. for 3 days and same overlay medium was added. Four days after infection, the cell sheets were washed with PBS and stained with 1.3% crystal violet in 95% ethanol. The antiviral efficacy of the compounds was expressed as the $IC_{50}$, that is the concentration of the compounds required to reduce the number of plaques to 50% in the control (virus-infected, but not untreated).

The compounds tested specifically inhibited the multiplication of HROV (Odelie) and SROV (SA11) as shown in Table IX.

TABLE IX

Anti-rotavirus activity

| | $IC_{50}$ (μg/mL) | |
|---|---|---|
| Compound | HRoV(Odelia) | SRoV(SA11) |
| A323 | 1.30 | 0.90 |
| B9 | 0.56 | 0.59 |

What is claimed is:
1. A substituted 1,4-dihydro-4-oxoquinline compound selected from the group consisting of:
 1,2-diphenyl-3-methyl-6-isopropyl- 1,4-dihydro-4-oxoquinoline,
 1-(2-fluorophenyl)-2-phenyl-3-methyl-6-isopropyl-1,4-dihydro-4-oxoquinoline,
 1-(3-fluorophenyl)-2-phenyl-3-methyl-6-isopropyl-1,4-dihydro-4-oxoquinoline,
 1-(4-fluorophenyl)-2-phenyl-3-methyl-6-isopropyl-1,4-dihydro-4-oxoquinoline,
 1-(4-chlorophenyl)-2-phenyl-3-methyl-6-isopropyl-1,4-dihydro-4-oxoquinoline,
 1-(4-tolyl)-2-phenyl-3-methyl-6-isopropyl-1,4-dihydro-4-osoquinoline, and
 1-(4-methoxyphenyl)-2-phenyl-3-methyl-6-isopropyl-1,4-dihydro-4-oxoquinline.

\* \* \* \* \*